(12) United States Patent
Berkelman

(10) Patent No.: US 8,664,396 B2
(45) Date of Patent: Mar. 4, 2014

(54) PHOTOLUMINESCENT METAL COMPLEXES FOR PROTEIN STAINING

(75) Inventor: Tom Berkelman, Oakland, CA (US)

(73) Assignee: Bio-Rad Laboratories, Inc., Hercule, CA (US)

( * ) Notice: Subject to any disclaimer, the term of this patent is extended or adjusted under 35 U.S.C. 154(b) by 741 days.

(21) Appl. No.: 12/274,979

(22) Filed: Nov. 20, 2008

(65) Prior Publication Data

US 2009/0131640 A1    May 21, 2009

Related U.S. Application Data

(60) Provisional application No. 61/004,115, filed on Nov. 21, 2007.

(51) Int. Cl.

| | |
|---|---|
| C07F 15/00 | (2006.01) |
| C07D 471/04 | (2006.01) |
| C07D 471/00 | (2006.01) |
| C07D 491/00 | (2006.01) |
| C07D 498/00 | (2006.01) |
| C07D 513/00 | (2006.01) |
| C07D 515/00 | (2006.01) |
| C07D 409/00 | (2006.01) |
| C07D 411/00 | (2006.01) |
| C07D 487/00 | (2006.01) |
| C07D 221/18 | (2006.01) |
| C07D 221/22 | (2006.01) |
| C07D 417/00 | (2006.01) |

(52) U.S. Cl.
USPC .......... 546/108; 546/4; 546/10; 546/88; 546/64; 546/281.1; 546/70; 546/77; 546/48; 548/159

(58) Field of Classification Search
USPC ............... 546/108, 80, 81, 101, 112, 135
See application file for complete search history.

(56) References Cited

U.S. PATENT DOCUMENTS

| | | | |
|---|---|---|---|
| 6,087,452 A | 7/2000 | Stewart et al. | |
| 6,316,267 B1 * | 11/2001 | Bhalgat et al. | 436/86 |
| 2005/0176624 A1 * | 8/2005 | Thompson et al. | 514/6 |
| 2008/0145526 A1 | 6/2008 | Mao et al. | |
| 2009/0093060 A1 | 4/2009 | Wong et al. | |

FOREIGN PATENT DOCUMENTS

| | | |
|---|---|---|
| DE | 102004022463 | 12/2005 |
| WO | 2004/043974 | 5/2004 |

OTHER PUBLICATIONS

Bolink, HJ. et al. Stabile-Layer Light-Emitting Electrochemical Cell Using 4,7-diphenyl-1,10-phenanthroline-bis(2-phenylpyridine)iridium(III) hexafluorophosphate. J. Am. Chem. Soc. 2006, vol. 128, p. 14787.*

Goldsmith, JI, et al. Discovery and High-Throughput Screening of Heteroleptic Iridium Complexes for Photoinduced Hydrogen Production. J. Am. Chem. Soc. 2005, vol. 127, p. 7505.*

Dragonetti, C. et al. The role of substituents of Functionalized 1,10-phenanthroline in controlling the emission properties of cationic iridium(III) complexes of interest for electroluminescent devices. Inorg. Chem. 2007, vol. 46, p. 8534.*

Lo, K. et al. Cyclometalated Iridium(III) diamine Bis(biotin) complexes as the first luminescent biotin-based cross-linkers for Avidin. Inorg. chem. 2007, vol. 46, p. 701.*

Bolink, HJ. et al. Stabile-Layer Light-Emitting Electrochemical Cell Using 4,7-diphenyl-1,10-phenanthroline-bis(2-phenylpyridine)iridium(III) hexafluorophosphate. J. Am. Chem. Soc. 2006, vol. 128, p. 14787, right column, second paragraph, line 3.*

Goldsmith, JI, et al. Discovery and High-Throughput Screening of Heteroleptic Iridium Complexes for Photoinduced Hydrogen Production. J. Am. Chem. Soc. 2005, vol. 127, p. 7505, top diagram and left column, second paragraph, last sentence.*

Dragonetti, C. et al. The role of substituents of Functionalized 1,10-phenanthroline in controlling the emission properties of cationic iridium(III) complexes of interest for electroluminescent devices. Inorg. Chem. 2007, vol. 46, p. 8534, right column, line 3-4, p. 8535, complex 3.*

Lo, K. et al. Cyclometalated Iridium(III) diamine Bis(biotin) complexes as the first luminescent biotin-based cross-linkers for Avidin. Inorg. chem. 2007, vol. 46, p. 701, scheme 1 and p. 704 figure 2.*

Ayala et al., "Synthesis Luminescence, and Excited-State Complexes of the Tris(1,10-phenanthroline)- and Bis(terpyridine)iridium(III) Cations," 1990, J. Am. Chem. Soc., 112, 3837-3844.

Bolink et al., "Stable single-layer light-emitting electrochemical cell using 4,7-diphenyl-1,10-phenanthroline-bis(2-phenylpyridine)iridium(III) hexafluorophosphate," 2006, 128, 14786-14787.

King et al., "Dual Emission from an Ortho-Metalated Ir(III) Complex," 1987, J. Am. Chem. Soc., 109, 1589-1590.

Lepeltier et al., "Synthesis, Structure and Photophysical and Electrochemical Properties of Cyclometallated Iridium (III) Complexes with Phenylated Bipyridine Ligands," 2005. Eur. J. Inorg. Chem., 110-117.

Lo et al. "Biological Labelling Reagents and Probes Derived from Luminescent Transition Metal Polypyridine Complexes," 2005, Coordination Chemistry Reviews, 249, 1434-1450.

(Continued)

Primary Examiner — Rita Desai
Assistant Examiner — Ben S Michelson
(74) Attorney, Agent, or Firm — Kilpatrick Townsend & Stockton LLP

(57) ABSTRACT

A method of staining a poly(amino acid) by contacting a poly(amino acid) with an overall neutral or overall cationic complex of at least one of transition metal ion, and a plurality of donor ligands each of which is fully coordinated to the transition metal ion and is either a nitrogen donor ligand or a cyclometalated donor ligand, such that at least one of the donor ligands is a cyclometalated donor ligand. Nitrogen donor ligands will contain heteroaryl ring systems having from 10 to 40 ring atoms, wherein each nitrogen donor ligand is substituted with from 0 to 4 $R^1$ groups. Cyclometalated donor ligands will likewise contain heteroaryl ring systems having from 10 to 40 ring atoms, such that at least one ring atom is N, wherein each cyclometalated donor ligand is substituted with from 0 to 4 $R^1$ groups. $R^1$, $R^2$, $R^3$ and $R^4$ groups are defined herein.

12 Claims, 5 Drawing Sheets

(56) References Cited

OTHER PUBLICATIONS

Lo et al., "First Examples of Luminescent Cyclometalated Iridium (III) Complexes as Labeling Reagents for Biological Substrates," 2001, Organometallies, 20, 4999-5001.

Ma et al., "A highly selective luminescent switch-on probe for histidine/histidine-rich proteins and its application in protein staining," 2008, Angew. Chem. Int. Ed., 47, 3735-3739.

Maeder et al., "Complexes of Rhodium (III) with Two Chelating CN Ligands and One Diimine Ligand," 1992, Helvetica Chimica Acta, vol. 75, 1320-1332.

Patton et al., "A thousand points of light: the application of fluorescence detection technologies to two-dimensional gel electrophoresis and proteomics," 2000, 21, 1123-1144.

Supplemental European Search Report dated May 27, 2011 issued in related European Application No. 08852114.1, filed Nov. 20, 2008.

Goldsmith et al., "Discovery and High-Throughput Screening of Heteroleptic Iridium Complexes for Photoinduced Hydrogen Production," 2005, J. Am. Chem. Soc., 127, 7502-7510.

Lowry et al., "Accelerated Luminophore Discovery through Combinatorial Synthesis," 2004, J. Am. Chem. Soc., 126, 14129-14135.

Lo et al., "Synthesis, photophysical and electrochemical properties, and protein-binding studies of luminescent cyclometalated iridium(III) bipyridine estradiol conjugates," 2007, Chem. Eur. J., 13, pp. 7110-7120.

Yu et al., "Cationic iridium(III) complexes for phosphorescence staining in the cytoplasm of living cells," 2008, Chem. Commun. pp. 2115-2117.

Lo, et al., "Synthesis, Photophysical and Electrochemical Properties, and Biological Labeling Studies of Cyclometalated Iridium (III) Bis(pyridylbenzaldehyde) Complexes: Novel Luminescent Cross-Linkers for Biomolecules," *Chem Eur J.*, vol. 9(2), pp. 475-483 (2003).

Lo, et al., "New Luminescent Cyclometalated Iridium(III) Diimine Complexes as Biological Labeling Reagents," *Inorg Chem.*, vol. 42(21), pp. 6886-6897 (2003).

Lo, et al., Synthesis, photophysical and electrochemical properties, and biological labeling studies of luminescent cyclometallated iridium(III) bipyridine-aldehyde complexes, *Inorganica Chimica Acta*, vol. 357, pp. 3109-3118 (2004).

Ohsawa, et al., "Electrochemistry and Spectroscopy of Ortho-Metalated Complexes of Ir(III) and Rh(III)," *J Phys Chem.*, vol. 91(5), pp. 1047-1054 (1987).

Sandrini, et al., "Spectroscopic and Electrochemical Properties of New Mixed-Ligand Orthometalated Rhodium(III) Complexes," *Inorg Chem.*, vol. 27, pp. 2640-2643 (1998).

Zhao, et al., "Series of New Cationic Iridium(III) Complexes with Tunable Emission Wavelength and Excited State Properties: Structures, Theoretical Calculations, and Photophysical and Electrochemical Properties," *Inorg Chem.*, vol. 45, pp. 6152-6160, (2006).

Japanese Office Action for Japanese Application No. 2010-535067, 6 pages, mailed May 28, 2013.

\* cited by examiner

A.

Compound 1

SYPRO Ruby

B.

Compound 1 ng/band

SYPRO Ruby ng/band

PHOTOLUMINESCENT METAL COMPLEXES FOR PROTEIN STAINING

CROSS-REFERENCES TO RELATED APPLICATIONS

This application claims priority to U.S. Provisional Application No. 61/004,115, filed Nov. 21, 2007, incorporated in its entirety herein by reference.

BACKGROUND OF THE INVENTION

Poly(amino acids), including peptides and proteins, are typically detected and characterized using gel electrophoresis, by solution quantitation assays or by detection on solid supports, such as filter membranes. Small amounts of protein or other poly(amino acids) are generally not visible to the naked eye, and must be stained before they can be localized and identified.

Two of the most common methods of staining poly(amino acids) in gels are COOMASSIE Brilliant Blue (CBB) staining and silver staining. For particular poly(amino acids), silver staining is approximately 100- to 1000-fold more sensitive than CBB staining, but both methods have disadvantages. In contrast, the use of luminescent reagents, such as fluorescent, phosphorescent or chemiluminescent reagents, for protein detection offers the possibility of greatly enhanced sensitivity and increased linear quantitation range, while simultaneously increasing the ease of use of the staining reagent.

The use of exemplary fluorescent stains, such a styryl and merocyanine dyes, for poly(amino acids) in gels (e.g. SYPRO® Red and SYPRO® Orange dyes of Invitrogen Corporation), on membranes or other supports, and in solution (U.S. Pat. No. 5,616,502 to Haugland et al., hereby incorporated by reference) is very rapid, relatively insensitive to poly(amino acid) composition, does not require destaining, and is more than an order of magnitude more sensitive than CBB staining.

Other fluorescent stains (e.g. SYPRO® Ruby [Invitrogen Corporation], Flamingo™ Fluorescent Gel Stain [Bio-Rad Laboratories], Deep Purple™ Total Protein Stain [GE Healthcare], Krypton™ Protein Stain [Pierce Biotechnology]) offer even better sensitivity, but require long multi-step staining procedures. These commercial fluorescent protein stains, with the exception of SYPRO Ruby, are excited relatively weakly by ultraviolet light. They are optimally imaged using visible light laser-based scanners as opposed to relatively simple and inexpensive instrumentation utilizing ultraviolet transillumination.

SUMMARY OF THE INVENTION

The present invention provides a method for staining poly (amino acids) using neutral or positively charged metal complexes. The metal complexes can have nitrogen donor ligands, cyclometalated ligands, or a mixture of the two. Use of the metal complexes of the present invention eliminates the need for de-staining and fixing of the poly(amino acids).

The transition metal complexes used to practice the method of the instant invention have an overall charge that is either neutral or cationic. The complexes are highly stable, even in dilute solution and associate strongly with proteins in electrophoretic gels, yielding bright, visible luminescence when excited with ultraviolet light. The instant metal complexes bind strongly and noncovalently to proteins, and provide poly(amino acid) detection of a higher sensitivity than other methods when used with ultraviolet excitation.

In one embodiment, the present invention provides a method of staining a poly(amino acid) that comprises contacting the poly(amino acid) with a metal complex having at least one transition metal ion, and a plurality of donor ligands each of which is fully coordinated to the transition metal ion and is either a nitrogen donor ligand or a cyclometalated donor ligand, such that at least one of the donor ligands is a cyclometalated donor ligand. Donor ligands in a single complex can be the same or different. Nitrogen donor ligands will contain heteroaryl ring systems having from 10 to 40 ring atoms, wherein from 2 to 8 ring atoms are N, O, S, or combinations thereof, such that at least two ring atoms are N, wherein each nitrogen donor ligand is substituted with from 0 to 4 $R^1$ groups. Cyclometalated donor ligands will likewise contain heteroaryl ring systems having from 10 to 40 ring atoms, wherein from 1 to 4 ring atoms are N, O, S or combinations thereof, such that at least one ring atom is N, wherein each cyclometalated donor ligand is substituted with from 0 to 4 $R^1$ groups. The $R^1$ groups are $C_{1-6}$ alkyl, $C_{2-6}$ alkenyl, $C_{2-6}$ alkynyl, $C_{1-6}$ alkoxy, halogen, $C_{1-6}$ haloalkyl, $-OR^2$, $-NR^2R^3$, $-CN$, $-C(O)R^2$, $-C(O)OR^2$, $-OC(O)R^2$, $-C(O)NR^2R^3$, $-N(R^2)C(O)R^3$, $-OC(O)NR^2R^3$, $-N(R^2)C(O)OR^3$, $-NR^2C(O)NR^3R^4$, $-NR^2C(S)NR^3R^4$, $-NO_2$, $=O$, aryl, heteroaryl, cycloalkyl or heterocycloalkyl. When two or more $R^1$ groups are present on a single donor ligand, they can be the same or different. The $R^2$, $R^3$ and $R^4$ groups are H or $C_{1-12}$ alkyl. Each of the $R^2$, $R^3$ and $R^4$ groups can be the same or different. Furthermore, the metal complex of the present invention is neutral or cationic in overall electronic charge, to achieve non-covalent association of said metal complex with the poly(amino acid). Thus, the metal complex stains the poly(amino acid).

In a second embodiment, the present invention provides a kit comprising a stock solution of a metal complex, as described above, a polar organic solvent, and either an acidic component, or an inorganic salt, or both. The metal complex can be present in a concentration from about 0.10 μM to about 10 μM. The kit of the present invention optionally further includes buffering agents, antioxidants, metal chelators, surfactants or additional detection reagents in the same or different solutions.

In a third embodiment, the present invention provides at least one transition metal ion and a plurality of donor ligands each fully coordinated to the transition metal ion and each independently a nitrogen donor ligand or a cyclometalated donor ligand, wherein at least one of the donor ligands is a cyclometalated donor ligand. Each nitrogen donor ligand comprises a heteroaryl ring system having from 10 to 40 ring atoms, wherein from 2 to 8 ring atoms are each independently N, O or S, wherein at least two ring atoms are N, and wherein each nitrogen donor ligand is substituted with from 0 to 4 $R^1$ groups. Each cyclometalated donor ligand comprises a heteroaryl ring system having from 10 to 40 ring atoms, wherein from 1 to 4 ring atoms are each independently N, O or S, wherein at least one ring atom is N, and wherein each cyclometalated donor ligand is substituted with from 0 to 4 $R^1$ groups. Each $R^1$ is independently $C_{1-6}$ alkyl, $C_{2-6}$ alkenyl, $C_{2-6}$ alkynyl, $C_{1-6}$ alkoxy, halogen, $C_{1-6}$ haloalkyl, $-OR^2$, $-NR^2R^3$, $-CN$, $-C(O)R^2$, $-C(O)OR^2$, $-OC(O)R^2$, $-C(O)NR^2R^3$, $-N(R^2)C(O)R^3$, $-OC(O)NR^2R^3$, $-N(R^2)C(O)OR^3$, $-NR^2C(O)NR^3R^4$, $-NR^2C(S)NR^3R^4$, $-NO_2$, $=O$, aryl, heteroaryl, cycloalkyl or heterocycloalkyl. Each $R^2$, $R^3$ and $R^4$ are independently H or $C_{1-12}$ alkyl. The metal complex is neutral or cationic in overall electronic charge. And when the cyclometalated donor ligand is phenylpyridine and the nitrogen donor ligand is bipyridyl, the nitrogen donor ligand is substituted with a group other than methyl.

BRIEF DESCRIPTION OF THE DRAWINGS

FIG. 2A shows the raw image, while FIG. 2B shows portions of the negative images that have been adjusted to show limit of sensitivity.

DETAILED DESCRIPTION OF THE INVENTION

I. Definitions

Figure 1:
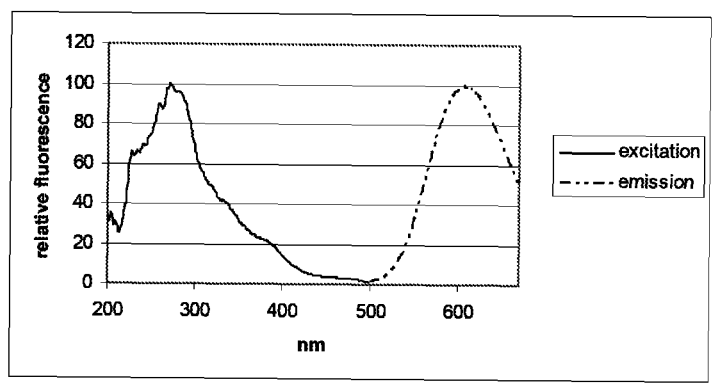
FIG. 1 shows the excitation and emission spectrum for compound 1.

As used herein, the term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid also refers to poly(amino acid) such as peptides, polypeptide and proteins.

"Amino acid analogs" refers to compounds that have the same basic chemical structure as a naturally occurring amino acid, i.e., an a carbon that is bound to a hydrogen, a carboxyl group, an amino group, and an R group. Examples of amino acid analogs include, but are not limited to, homoserine, norleucine, methionine sulfoxide, methionine methyl sulfonium. Such analogs have modified R groups (e.g., norleucine) or modified peptide backbones, but retain the same basic chemical structure as a naturally occurring amino acid.

"Unnatural amino acids" are not encoded by the genetic code and can, but do not necessarily, have the same basic structure as a naturally occurring amino acid. Unnatural amino acids include, but are not limited to, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, ornithine, pentylglycine, pipecolic acid and thioproline.

"Amino acid mimetics" refers to chemical compounds that have a structure that is different from the general chemical structure of an amino acid, but that functions in a manner similar to a naturally occurring amino acid.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid (i.e., hydrophobic, hydrophilic, positively charged, neutral, negatively charged). Exemplified hydrophobic amino acids include valine, leucine, isoleucine, methionine, phenylalanine, and tryptophan. Exemplified aromatic amino acids include phenylalanine, tyrosine and tryptophan. Exemplified aliphatic amino acids include serine and threonine. Exemplified basic aminoacids include lysine, arginine and histidine. Exemplified amino acids with carboxylate side-chains include aspartate and glutamate. Exemplified amino acids with carboxamide side chains include asparagines and glutamine. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

As used herein, the term "contacting" refers to the process of bringing into contact at least two distinct species such that they can react. It should be appreciated, however, the resulting reaction product can be produced directly from a reaction between the added reagents or from an intermediate from one or more of the added reagents which can be produced in the reaction mixture.

As used herein, the term "transition metal ion" refers to transition metals of the periodic table that are positively charged as a result of having fewer electrons in the valence shell than is present for the neutral transition metal. Transition metals include Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, Hg and Ac. One of skill in the art will appreciate that the transition metals described above can each adopt several different oxidation states, all of which are useful in the present invention. In some instances, the most stable oxidation state is formed, but other oxidation states are useful in the present invention. Transition metal ions useful in the present invention include, but are not limited to, Ir (III) and Rh (III).

As used herein, the term "coordinated" refers to the formation of a bond between an atom donating electrons and an atom accepting electrons where both electrons shared in the bond come from a single atom, the donor atom.

As used herein, the term "donor ligand" refers to a ligand that donates one or more of its electrons through a coordinate bond (where both electrons shared in a bond come from the same atom) to one or more central atoms or ions, such as a transition metal ion. The electrons from the donor ligand can be lone pair electrons, such as on a nitrogen, oxygen, sulfur or phosphorus, for example. Alternatively, the electrons from the donor ligand can be from an anion, such as a carbanion and an oxygen anion. When the lone pair of electrons is donated from only nitrogen atoms, then the ligand is a nitrogen donor ligand. Multidentate ligands are ligands containing more than one atom coordinately bonded to a single transition metal ion. When the donor ligand is multidentate and at least one coordinating atom is carbon such that a covalent bond is formed between the metal and the carbon, then the ligand is a cyclometalated ligand. Cyclometalated complexes are complexes between at least one cyclometalated ligand and at least one transition metal ion. Cyclometalated complexes are formed through the loss of a proton at the site of carbon-metal coordination and a change in the charge of the complex of −1 per carbon-metal bond formed. Cyclometalated ligands are therefore formally described as comprising a carbanion at the site of carbon-metal coordination. One of skill in the art will appreciate that other donor ligands are useful in the present invention.

As used herein, the term "heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, benzoxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred, 4-thiazolyl. Triazolyl is preferably 1-, 2- or 5-(1,2,4-triazolyl). Tetrazolyl is preferably 5-tetrazolyl. Additional heteroaryl compounds include, but are not limited to, chromenone, chromone and coumarin.

Preferably, heteroaryl is pyridyl, indolyl, quinolinyl, pyrrolyl, thiazolyl, isoxazolyl, triazolyl, tetrazolyl, pyrazolyl, imidazolyl, thienyl, furanyl, benzothiazolyl, benzoxazolyl, benzofuranyl, isoquinolinyl, benzothienyl, oxazolyl, indazolyl, 2-oxo-2H-chromenyl, or any of the radicals substituted, especially mono- or di-substituted.

As used herein, the term "alkyl" refers to a straight or branched, saturated, aliphatic radical having the number of carbon atoms indicated. For example, $C_1$-$C_6$ alkyl includes, but is not limited to, methyl, ethyl, propyl, butyl, pentyl, hexyl, iso-propyl, iso-butyl, sec-butyl, tert-butyl, etc.

The term "lower" referred to above and hereinafter in connection with organic radicals or compounds respectively defines a compound or radical which can be branched or unbranched with from 1 to 7, preferably from 1 to 4 carbon atoms, and (as unbranched) one or two carbon atoms.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to (2 m'+1), where m' is the total number of carbon atoms in such radical. R', R" and R'" each independently refer to hydrogen, unsubstituted ($C_1$-$C_8$)alkyl and heteroalkyl, unsubstituted aryl, unsubstituted alkyl, alkoxy or thioalkoxy groups, or unsubstituted aryl-($C_1$-$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like). Preferably, the substituted alkyl and heteroalkyl groups have from 1 to 4 substituents, more preferably 1, 2 or 3 substituents. Exceptions are those perhalo alkyl groups (e.g., pentafluoroethyl and the like) which are also preferred and contemplated by the present invention.

As used herein, the term "alkenyl" refers to either a straight chain or branched hydrocarbon of 2 to 6 carbon atoms, having at least one double bond. Examples of alkenyl groups include, but are not limited to, vinyl, propenyl, isopropenyl, butenyl, isobutenyl, butadienyl, pentenyl or hexadienyl.

As used herein, the term "alkynyl" refers to either a straight chain or branched hydrocarbon of 2 to 6 carbon atoms, having at least one triple bond. Examples of alkynyl groups include, but are not limited to, acetylenyl, propynyl or butynyl.

As used herein, the term "alkoxy" refers to alkyl with the inclusion of an oxygen atom, for example, methoxy, ethoxy, etc. "Halo-substituted-alkoxy" is as defined for alkoxy where some or all of the hydrogen atoms are substituted with halogen atoms. For example, halo-substituted-alkoxy includes trifluoromethoxy, etc.

As used herein, the term "halogen" refers to fluorine, chlorine, bromine and iodine.

As used herein, the term "haloalkyl" refers to alkyl as defined above where some or all of the hydrogen atoms are substituted with halogen atoms. Halogen (halo) preferably represents chloro or fluoro, but may also be bromo or iodo. For example, haloalkyl includes trifluoromethyl, fluoromethyl, 1,2,3,4,5-pentafluoro-phenyl, etc. The term "perfluoro" defines a compound or radical which has at least two available hydrogens substituted with fluorine. For example, perfluorophenyl refers to 1,2,3,4,5-pentafluorophenyl, perfluoromethane refers to 1,1,1-trifluoromethyl, and perfluoromethoxy refers to 1,1,1-trifluoromethoxy.

As used herein, the term "aryl" refers to a monocyclic or fused bicyclic, tricyclic or greater, aromatic ring assembly containing 6 to 16 ring carbon atoms. For example, aryl may be phenyl, benzyl or naphthyl, preferably phenyl. "Arylene" means a divalent radical derived from an aryl group. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

Preferred as aryl is naphthyl, phenyl or phenyl mono- or disubstituted by alkoxy, phenyl, halogen, alkyl or trifluoromethyl, especially phenyl or phenyl-mono- or disubstituted by alkoxy, halogen or trifluoromethyl, and in particular phenyl.

Examples of substituted phenyl groups as R are, e.g. 4-chlorophen-1-yl, 3,4-dichlorophen-1-yl, 4-methoxyphen-1-yl, 4-methylphen-1-yl, 4-aminomethylphen-1-yl, 4-methoxyethylaminomethylphen-1-yl, 4-hydroxyethylaminomethylphen-1-yl, 4-hydroxyethyl-(methyl)-aminomethylphen-1-yl, 3-aminomethylphen-1-yl, 4-N-acetylaminomethylphen-1-yl, 4-aminophen-1-yl, 3-aminophen-1-yl, 2-aminophen-1-yl, 4-phenyl-phen-1-yl, 4-(imidazol-1-yl)-phen-yl, 4-(imidazol-1-ylmethyl)-phen-1-yl, 4-(morpholin-1-yl)-phen-1-yl, 4-(morpholin-1-ylmethyl)-phen-1-yl, 4-(2-methoxyethylaminomethyl)-phen-1-yl and 4-(pyrrolidin-1-ylmethyl)-phen-1-yl, 4-(thiophenyl)-phen-1-yl, 4-(3-thiophenyl)-phen-1-yl, 4-(4-methylpiperazin-1-yl)-phen-1-yl, and 4-(piperidinyl)-phenyl and 4-(pyridinyl)-phenyl optionally substituted in the heterocyclic ring.

Similarly, substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR"C(NH$_2$)=NH, —NH—C(NH$_2$)=NR', —S(O)R', —S(O)$_2$R', —S(O)$_2$NR"R", —N$_3$, —CH(Ph)$_2$, perfluoro($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, unsubstituted ($C_1$-$C_8$)alkyl and unsubstituted heteroalkyl, unsubstituted aryl and unsubstituted heteroaryl, unsubstituted (aryl)-($C_1$-$C_4$)alkyl, and unsubstituted (aryl)oxy-($C_1$-$C_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 4, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted ($C_1$-$C_6$)alkyl.

As used herein, the term "cycloalkyl" refers to a saturated or partially unsaturated, monocyclic, fused bicyclic or bridged polycyclic ring assembly containing from 3 to 12 ring atoms, or the number of atoms indicated. For example, $C_{3-8}$cycloalkyl includes cyclopropyl, cyclobutyl, cyclopentyl, cyclohexyl, and up to cyclooctyl.

As used herein, the term "heterocycle" refers to a ring system having from 3 ring members to about 20 ring members and from 1 to about 5 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heterocycle includes, but is not limited to, tetrahydrofuranyl, tetrahydrothiophenyl, morpholino, pyrrolidinyl, pyrrolinyl, imidazolidinyl, imidazolinyl, pyrazolidinyl, pyrazolinyl, piperazinyl, piperidinyl, indolinyl, quinuclidinyl and 1,4-dioxa-8-aza-spiro[4.5]dec-8-yl.

As used herein, the term "associated" refers to two molecular entities stably bound to each other without implying the physical basis of the bond.

As used herein, the term "overall electronic charge" refers to the charge on the complex, taking into consideration the charges on the transition metal ion and each ligand without accounting for the charge of any counter-ion present As used herein, the term "polar solvent" refers to solvents useful for dissolving polar compounds and capable of forming a single phase mixture with water. Polar solvents useful in the present invention include, but are not limited to, water, alcohols such as methanol, ethanol, propanol, isopropanol, butanol, sec-butanol, isobutanol, tert-butanol, ethylene glycol, propylene glycol, glycerol, in addition to dimethyl sulfoxide, dimethyl formamide, sulfolane, methyl formamide, dimethylacetamide, methylacetamide, formamide, methylpyrrolidone, pyrrolidone, and dimethylimidazolinone.

II. Metal Complexes of the Present Invention

The metal complexes of the present invention can include nitrogen donor ligands, cyclometalated donor ligands and transition metal ions. In some embodiments, the metal complexes of the present invention include at least one transition metal ion, and a plurality of donor ligands each fully coordinated to the transition metal ion, wherein each donor ligand is a nitrogen donor ligand or a cyclometalated donor ligand, such that at least one of the donor ligands is a cyclometalated donor ligand. Each donor ligand can be the same or different. Nitrogen donor ligands will contain heteroaryl ring systems having from 10 to 40 ring atoms, wherein from 2 to 8 ring atoms are N, O, S, or combinations thereof, such that at least two ring atoms are N, wherein each nitrogen donor ligand is substituted with from 0 to 4 R'groups. Cyclometalated donor ligands will likewise contain heteroaryl ring systems having from 10 to 40 ring atoms, wherein from 1 to 4 ring atoms are N, O, S or combinations thereof, such that at least one ring atom is N, wherein each cyclometalated donor ligand is substituted with from 0 to 4 R'groups. The $R^1$ groups are $C_{1-6}$ alkyl, $C_{2-6}$ alkenyl, $C_{2-6}$ alkynyl, $C_{1-6}$ alkoxy, halogen, $C_{1-6}$ haloalkyl, —OR$^2$, —NR$^2$R$^3$, —CN, —C(O)R$^2$, —C(O)OR$^2$, —OC(O)R$^2$, —C(O)NR$^2$R$^3$, —N(R$^2$)C(O)R$^3$, —OC(O)

NR$^2$R$^3$, —N(R$^2$)C(O)OR$^3$, —NR$^2$C(O)NR$^3$R$^4$, —NR$^2$C(S)NR$^1$R$^4$, —NO$_2$, =O, aryl, heteroaryl, cycloalkyl or heterocycloalkyl. When two or more R$^1$ groups are present on a single donor ligand, they can be the same or different. The R$^2$, R$^3$ and R$^4$ groups are H or C$_{1-12}$ alkyl. Each of the R$^2$, R$^3$ and R$^4$ groups can be the same or different. Alternatively, R' groups can combine with each other to form aryl and heteroaryl groups.

A. Nitrogen Donor Ligands

The nitrogen donor ligands useful in the method of the present invention can be any nitrogen donor ligand that has two nitrogen donor atoms available to bind to a metal. The metal complexes of the present invention can have any number of nitrogen donor ligands. In some embodiments, the metal complexes can have 0, 1 or 2 nitrogen donor ligands. When two or more nitrogen donor ligands are present in a single metal complex, they can be the same or different.

In some embodiments, each nitrogen donor ligand of the present invention will have a heteroaryl ring system having from 10 to 40 ring atoms, where from 2 to 8 ring atoms can each be N, O or S, wherein at least two ring atoms are N, substituted with from 0 to 4 R$^1$ groups. In other embodiments, each nitrogen donor ligand has the formula:

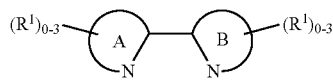

wherein rings A and B can each have from 5 to 20 ring atoms, where from 1 to 4 ring atoms can each be N, O or S, wherein at least one ring atom is N. In some other embodiments, each nitrogen donor ligand can be:

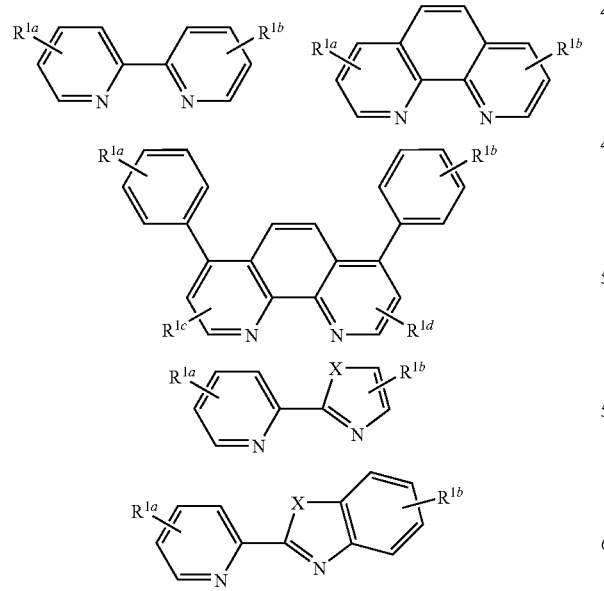

wherein each of R$^{1a}$, R$^{1b}$, R$^{1c}$ and R$^{1d}$ are as defined above for R$^1$, and X is an optionally substituted methylene, O, S, —NR$^2$ and Se.

In another embodiment, each nitrogen donor ligand can be:

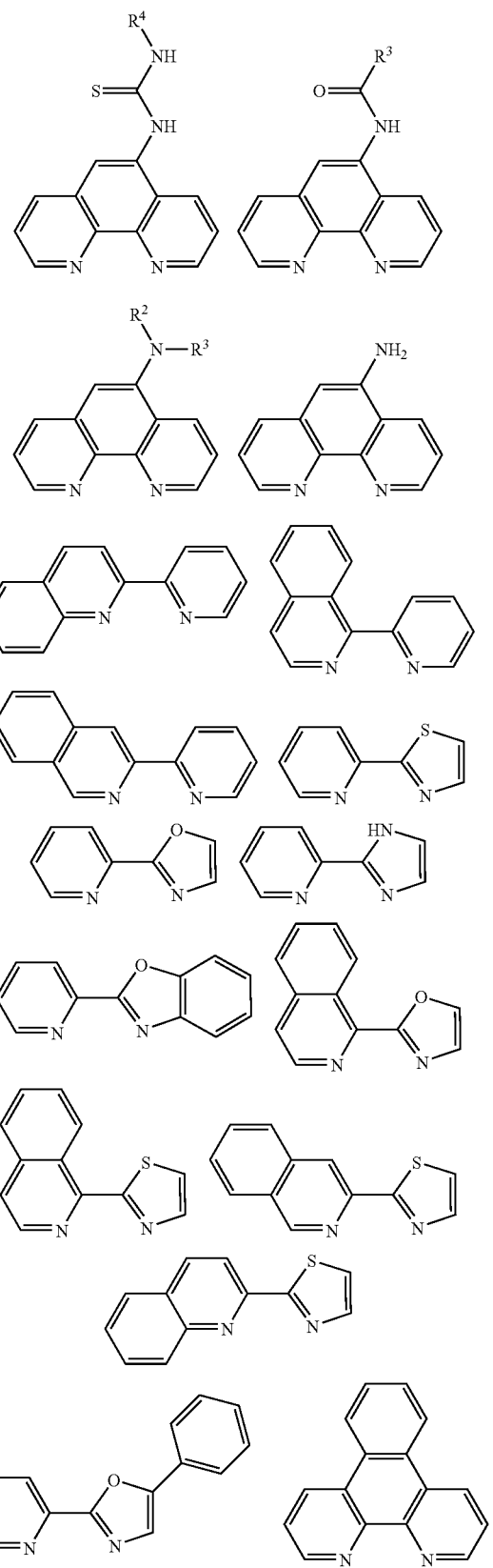

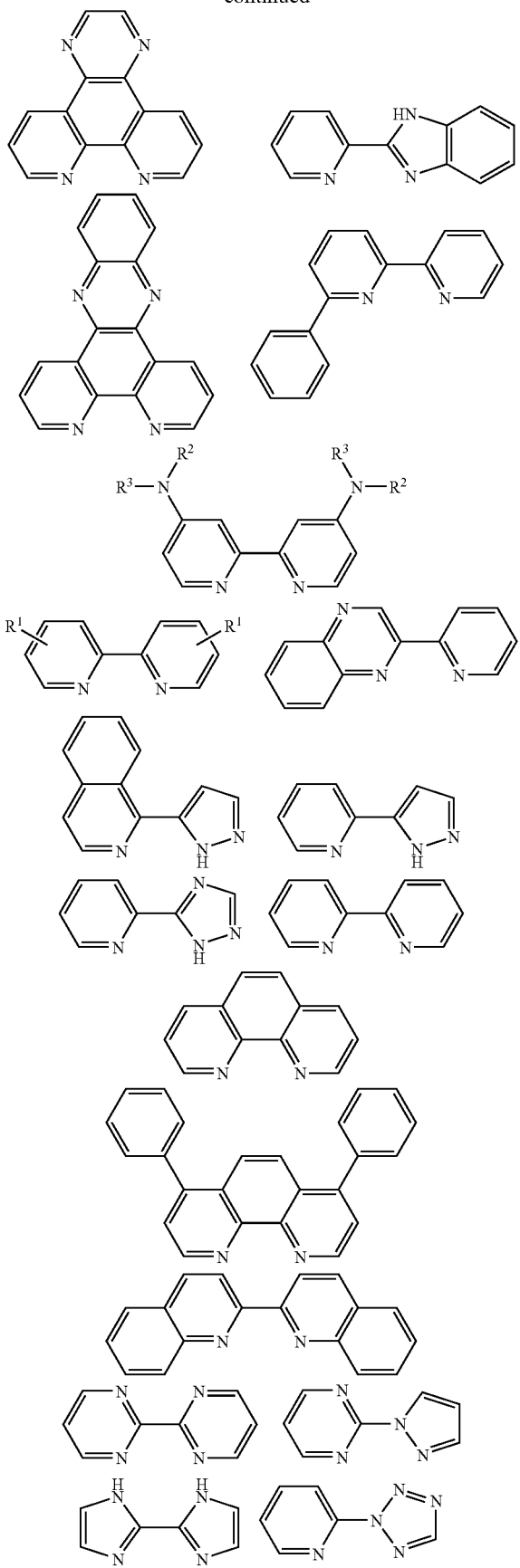

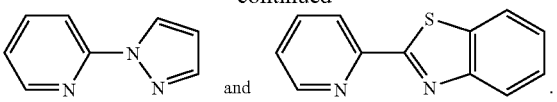

In some embodiments, each nitrogen donor ligand can be:

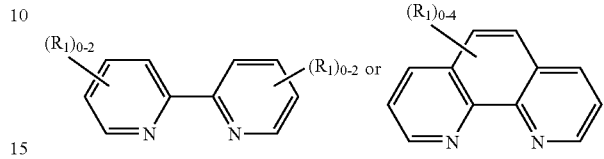

In some other embodiments, $R^1$ can be $C_{1-6}$ alkyl, $-NR^2R^3$, $-N(R^2)C(O)R^3$, $-NR^2C(O)NR^3R^4$, $-NR^2C(S)NR^3R^4$ or phenyl. Each R' can be the same or different. In other embodiments, each nitrogen donor ligand has the formula:

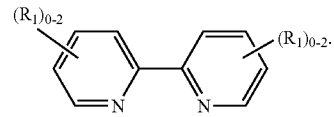

In another embodiment, each nitrogen donor ligand has the formula:

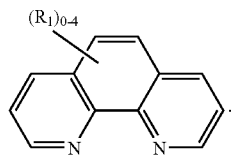

One of skill in the art will appreciate that other nitrogen donor ligands are useful in the present invention.

B. Cyclometalated Donor Ligands

The cyclometalated donor ligands useful in the method of the present invention can be any cyclometalated donor ligand that has one nitrogen donor atom and one carbanion available to bind to a metal. The metal complexes of the present invention can have any number of cyclometalated donor ligands. In some embodiments, the metal complexes can have 1, 2 or 3 cyclometalated donor ligands. When two or more cyclometalated donor ligands are present in a single metal complex, they can be the same or different.

In some embodiments, each cyclometalated donor ligand will have a heteroaryl ring system having from 10 to 40 ring atoms, where from 1 to 4 ring atoms can each be N, O or S, wherein at least one ring atom is N, substituted with from 0 to 4 $R^1$ groups. In other embodiments, each cyclometalated donor ligand is a cyclometalated donor ligand of the formula:

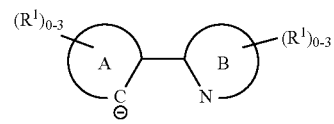

wherein ring A can be an aryl ring system having 6-15 ring atoms or a heteroaryl ring system having from 5-15 ring atoms, where from 1 to 4 ring atoms of the heteroaryl ring system can each be N, O or S; and ring B is a heteroaryl ring system having from 5 to 20 ring atoms, where from 1 to 4 ring atoms can each be N, O or S, wherein at least one ring atom is N. In still other embodiments, the cyclometalated ligand can be:

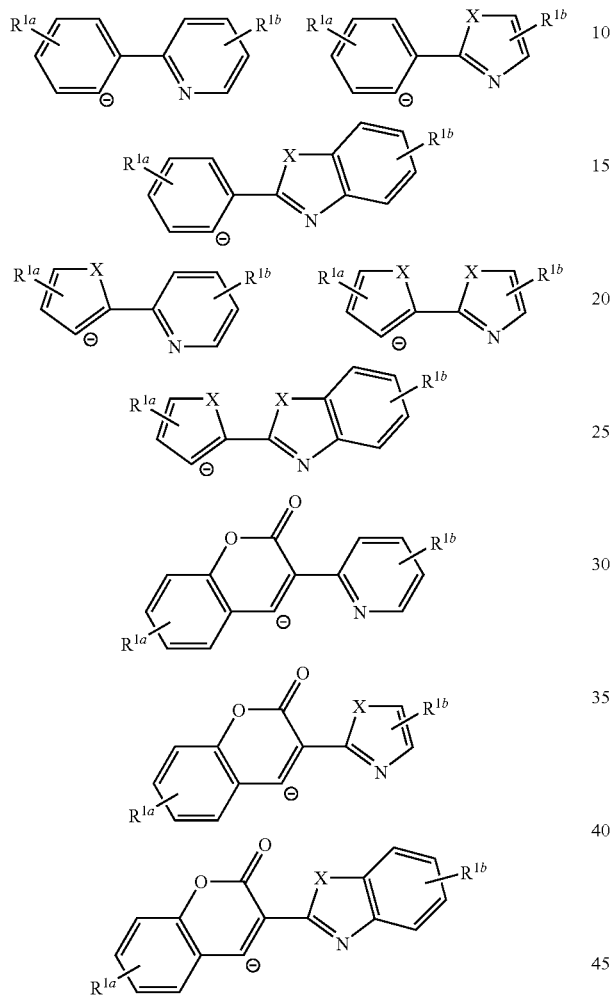

wherein each of $R^{1a}$ and $R^{1b}$ are as defined above for $R^1$, and X is an optionally substituted methylene, O, S, —$NR^2$ and Se.

In another embodiment, each cyclometalated ligand can be:

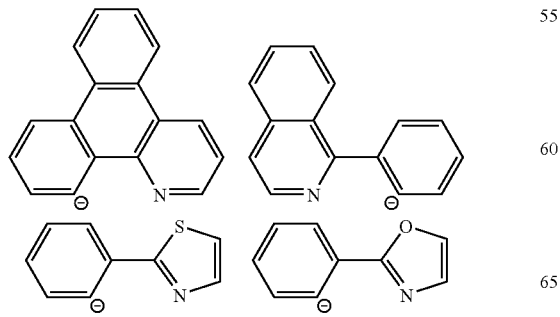

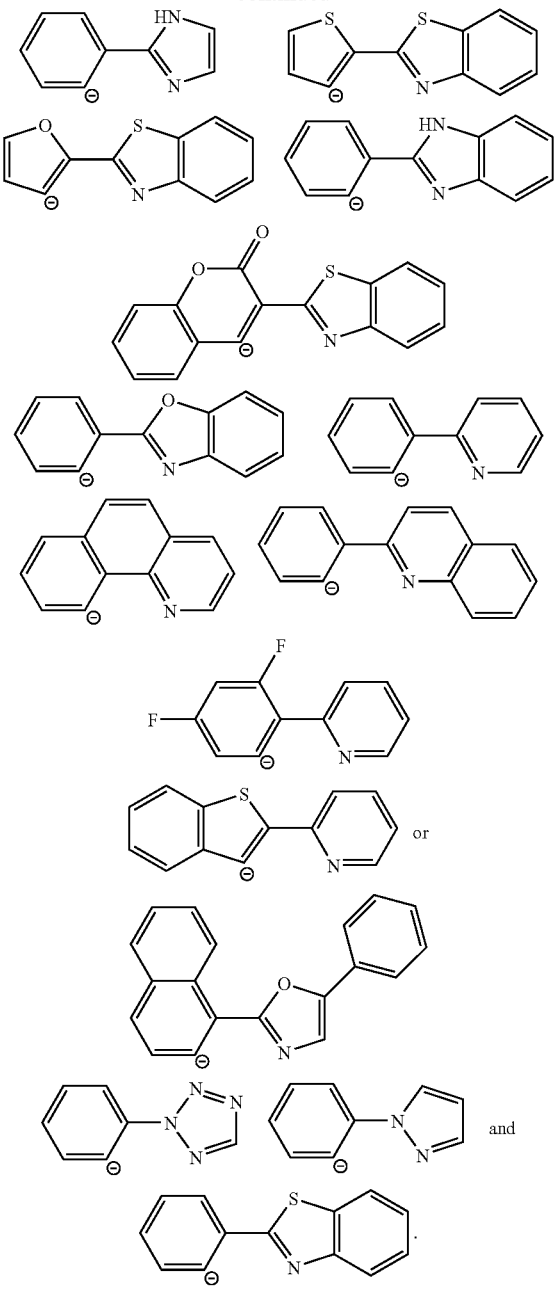

In some embodiments, each cyclometalated ligand can be:

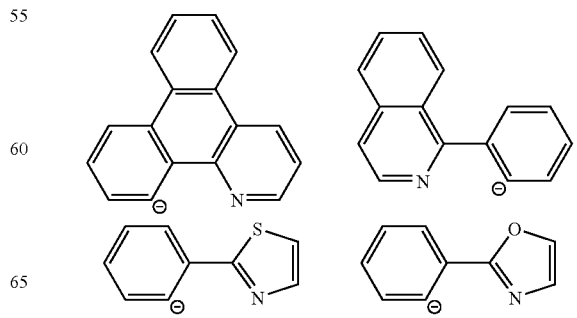

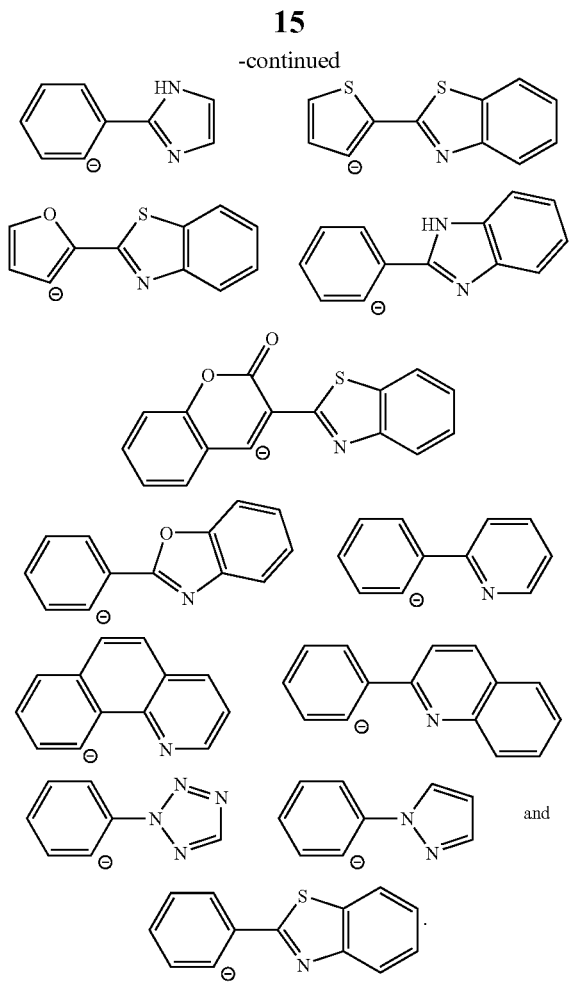

In other embodiments, the cyclometalated donor ligand can be:

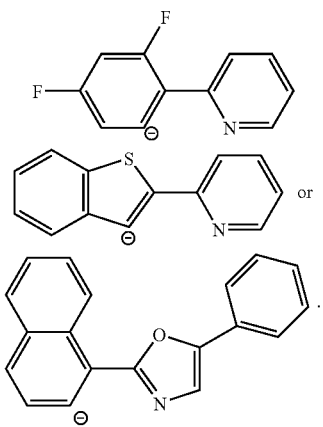

In some embodiments, the cyclometalated donor ligand can be

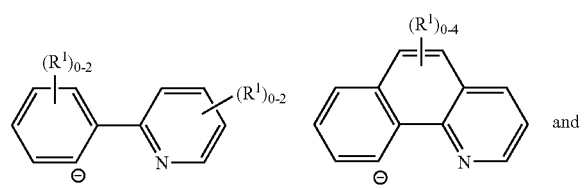

Each cyclometalated donor ligand can be the same or different. In some other embodiments, $R^1$ can be $C_{1-6}$ alkyl, $-NR^2R^3$, $-N(R^2)C(O)R^3$, $-NR^2C(O)NR^3R^4$, $-NR^2C(S)NR^3R^4$ or phenyl. Each $R^1$ can be the same or different.

One of skill in the art will appreciate that other cyclometalated ligands are useful in the present invention.

C. Transition Metal Ions

Transition metal ions useful in the metal complexes of the present invention can be any transition metal. Transition metals that are useful in the present invention include Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, Hg and Ac. One of skill in the art will appreciate that the transition metals described above can each adopt several different oxidation states, all of which are useful in the present invention. In some instances, the most stable oxidation state is formed, but other oxidation states are useful in the present invention.

In some embodiments, the transition metal ion can be Ir, Rh, Os, Pt, Ru, Pd or Re. In another embodiment, the transition metal ion can be Ir. In other embodiments, the transition metal ion can be Ir(III). In some other embodiments, the transition metal ion can be Rh. In still other embodiments, the transition metal ion can be Rh(III). One of skill in the art will appreciate that other metals and oxidation states are useful in the present invention.

D. Metal Complexes

The metal complexes of the present invention can include the nitrogen donor ligands, the cyclometalated donor ligands and the transition metal ions defined above.

In other embodiments, the metal complex is neutral or cationic in overall electronic charge. In still other embodiments, the metal complexes include those described above with the proviso that when the cyclometalated donor ligand is phenylpyridine and the nitrogen donor ligand is bipyridyl, the nitrogen donor ligand is substituted with a group other than methyl.

In some other embodiments, the nitrogen donor ligand is phenanthroline or bipyridyl. In still other embodiments, the nitrogen donor ligand is phenanthroline. In yet other embodiments, the nitrogen donor ligand is bipyridyl. In still yet other embodiments, the metal complex has one nitrogen donor ligand and two cyclometalated donor ligands, wherein the nitrogen donor ligand is phenanthroline or bipyridyl, where the nitrogen donor ligand is substituted with at least two phenyl groups.

In other embodiments, the metal complex of the present invention is cationic in overall electronic charge. In some other embodiments, the metal complex can have one nitrogen donor ligand and two cyclometalated donor ligands. In still other embodiments, the metal complex can have two nitrogen donor ligands and one cyclometalated donor ligand.

In some embodiments, the metal complexes of the present invention can include at least one cyclometalated donor ligand and at least one nitrogen donor ligand, such as the compounds described in the table below.

TABLE 1

Photoluminescent Metal Complexes

| Compound | Nitrogen Donor Ligand | Cyclometalated Donor Ligand | Metal |
|---|---|---|---|
| 1 | A | (I)$_2$ | Ir$^{3+}$ |
| 2 | A | (II)$_2$ | Ir$^{3+}$ |
| 3 | A | (III)$_2$ | Ir$^{3+}$ |
| 4 | A | (IV)$_2$ | Ir$^{3+}$ |
| 5 | A | (V)$_2$ | Ir$^{3+}$ |
| 6 | A | (VI)$_2$ | Ir$^{3+}$ |
| 7 | A | (VII)$_2$ | Ir$^{3+}$ |
| 8 | A | (VIII)$_2$ | Ir$^{3+}$ |
| 9 | A | (IX)$_2$ | Ir$^{3+}$ |
| 10 | B | (I)$_2$ | Ir$^{3+}$ |
| 11 | B | (II)$_2$ | Ir$^{3+}$ |
| 12 | B | (III)$_2$ | Ir$^{3+}$ |
| 13 | B | (IV)$_2$ | Ir$^{3+}$ |
| 14 | B | (V)$_2$ | Ir$^{3+}$ |
| 15 | B | (VI)$_2$ | Ir$^{3+}$ |
| 16 | B | (VII)$_2$ | Ir$^{3+}$ |
| 17 | B | (VIII)$_2$ | Ir$^{3+}$ |
| 18 | B | (IX)$_2$ | Ir$^{3+}$ |
| 19 | C | (I)$_2$ | Ir$^{3+}$ |
| 20 | C | (II)$_2$ | Ir$^{3+}$ |
| 21 | C | (III)$_2$ | Ir$^{3+}$ |
| 22 | C | (IV)$_2$ | Ir$^{3+}$ |
| 23 | C | (V)$_2$ | Ir$^{3+}$ |
| 24 | C | (VI)$_2$ | Ir$^{3+}$ |
| 25 | C | (VII)$_2$ | Ir$^{3+}$ |
| 26 | C | (VIII)$_2$ | Ir$^{3+}$ |
| 27 | C | (IX)$_2$ | Ir$^{3+}$ |
| 28 | D | (I)$_2$ | Ir$^{3+}$ |
| 29 | D | (II)$_2$ | Ir$^{3+}$ |
| 30 | D | (III)$_2$ | Ir$^{3+}$ |
| 31 | D | (IV)$_2$ | Ir$^{3+}$ |
| 32 | D | (V)$_2$ | Ir$^{3+}$ |
| 33 | D | (VI)$_2$ | Ir$^{3+}$ |
| 34 | D | (VII)$_2$ | Ir$^{3+}$ |
| 35 | D | (VIII)$_2$ | Ir$^{3+}$ |
| 36 | D | (IX)$_2$ | Ir$^{3+}$ |
| 37 | E | (I)$_2$ | Ir$^{3+}$ |
| 38 | E | (II)$_2$ | Ir$^{3+}$ |
| 39 | E | (III)$_2$ | Ir$^{3+}$ |
| 40 | E | (IV)$_2$ | Ir$^{3+}$ |
| 41 | E | (V)$_2$ | Ir$^{3+}$ |
| 42 | E | (VI)$_2$ | Ir$^{3+}$ |
| 43 | E | (VII)$_2$ | Ir$^{3+}$ |
| 44 | E | (VIII)$_2$ | Ir$^{3+}$ |
| 45 | E | (IX)$_2$ | Ir$^{3+}$ |
| 46 | F | (I)$_2$ | Ir$^{3+}$ |
| 47 | F | (II)$_2$ | Ir$^{3+}$ |
| 48 | F | (III)$_2$ | Ir$^{3+}$ |
| 49 | F | (IV)$_2$ | Ir$^{3+}$ |
| 50 | F | (V)$_2$ | Ir$^{3+}$ |
| 51 | F | (VI)$_2$ | Ir$^{3+}$ |
| 52 | F | (VII)$_2$ | Ir$^{3+}$ |
| 53 | F | (VIII)$_2$ | Ir$^{3+}$ |
| 54 | F | (IX)$_2$ | Ir$^{3+}$ |
| 55 | A | (I)$_2$ | Rh$^{3+}$ |
| 56 | A | (II)$_2$ | Rh$^{3+}$ |
| 57 | A | (III)$_2$ | Rh$^{3+}$ |
| 58 | A | (IV)$_2$ | Rh$^{3+}$ |
| 59 | A | (V)$_2$ | Rh$^{3+}$ |
| 60 | A | (VI)$_2$ | Rh$^{3+}$ |
| 61 | A | (VII)$_2$ | Rh$^{3+}$ |
| 62 | A | (VIII)$_2$ | Rh$^{3+}$ |
| 63 | A | (IX)$_2$ | Rh$^{3+}$ |
| 64 | B | (I)$_2$ | Rh$^{3+}$ |
| 65 | B | (II)$_2$ | Rh$^{3+}$ |
| 66 | B | (III)$_2$ | Rh$^{3+}$ |
| 67 | B | (IV)$_2$ | Rh$^{3+}$ |
| 68 | B | (V)$_2$ | Rh$^{3+}$ |
| 69 | B | (VI)$_2$ | Rh$^{3+}$ |
| 70 | B | (VII)$_2$ | Rh$^{3+}$ |
| 71 | B | (VIII)$_2$ | Rh$^{3+}$ |
| 72 | B | (IX)$_2$ | Rh$^{3+}$ |
| 73 | C | (I)$_2$ | Rh$^{3+}$ |
| 74 | C | (II)$_2$ | Rh$^{3+}$ |
| 75 | C | (III)$_2$ | Rh$^{3+}$ |
| 76 | C | (IV)$_2$ | Rh$^{3+}$ |
| 77 | C | (V)$_2$ | Rh$^{3+}$ |
| 78 | C | (VI)$_2$ | Rh$^{3+}$ |
| 79 | C | (VII)$_2$ | Rh$^{3+}$ |
| 80 | C | (VIII)$_2$ | Rh$^{3+}$ |
| 81 | C | (IX)$_2$ | Rh$^{3+}$ |
| 82 | D | (I)$_2$ | Rh$^{3+}$ |
| 83 | D | (II)$_2$ | Rh$^{3+}$ |
| 84 | D | (III)$_2$ | Rh$^{3+}$ |
| 85 | D | (IV)$_2$ | Rh$^{3+}$ |
| 86 | D | (V)$_2$ | Rh$^{3+}$ |
| 87 | D | (VI)$_2$ | Rh$^{3+}$ |
| 88 | D | (VII)$_2$ | Rh$^{3+}$ |
| 89 | D | (VIII)$_2$ | Rh$^{3+}$ |
| 90 | D | (IX)$_2$ | Rh$^{3+}$ |
| 91 | E | (I)$_2$ | Rh$^{3+}$ |
| 92 | E | (II)$_2$ | Rh$^{3+}$ |
| 93 | E | (III)$_2$ | Rh$^{3+}$ |
| 94 | E | (IV)$_2$ | Rh$^{3+}$ |
| 95 | E | (V)$_2$ | Rh$^{3+}$ |
| 96 | E | (VI)$_2$ | Rh$^{3+}$ |
| 97 | E | (VII)$_2$ | Rh$^{3+}$ |
| 98 | E | (VIII)$_2$ | Rh$^{3+}$ |
| 99 | E | (IX)$_2$ | Rh$^{3+}$ |
| 100 | F | (I)$_2$ | Rh$^{3+}$ |
| 101 | F | (II)$_2$ | Rh$^{3+}$ |
| 102 | F | (III)$_2$ | Rh$^{3+}$ |
| 103 | F | (IV)$_2$ | Rh$^{3+}$ |
| 104 | F | (V)$_2$ | Rh$^{3+}$ |
| 105 | F | (VI)$_2$ | Rh$^{3+}$ |
| 106 | F | (VII)$_2$ | Rh$^{3+}$ |
| 107 | F | (VIII)$_2$ | Rh$^{3+}$ |
| 108 | F | (IX)$_2$ | Rh$^{3+}$ |

Nitrogen Donor Ligands

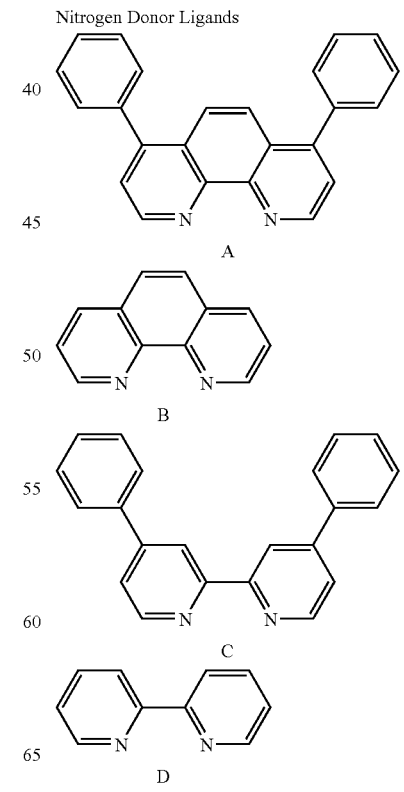

TABLE 1-continued

Photoluminescent Metal Complexes

| Compound | Nitrogen Donor Ligand | Cyclometalated Donor Ligand | Metal |
|---|---|---|---|

E

F

Cyclometalated Donor Ligands

I

II

III

IV

V

VI

VII

VIII

IX

In a further embodiment, the metal complex can be

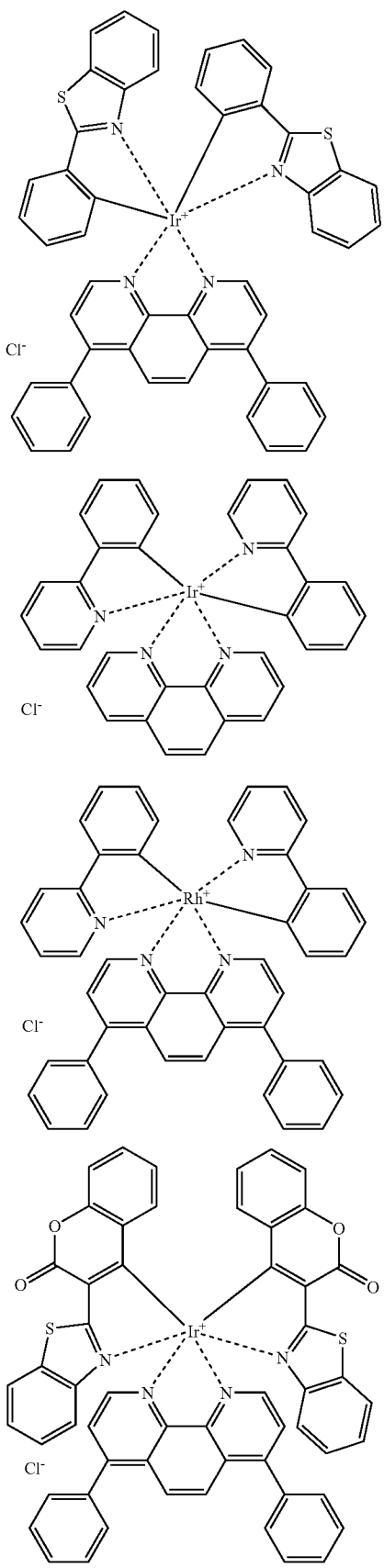
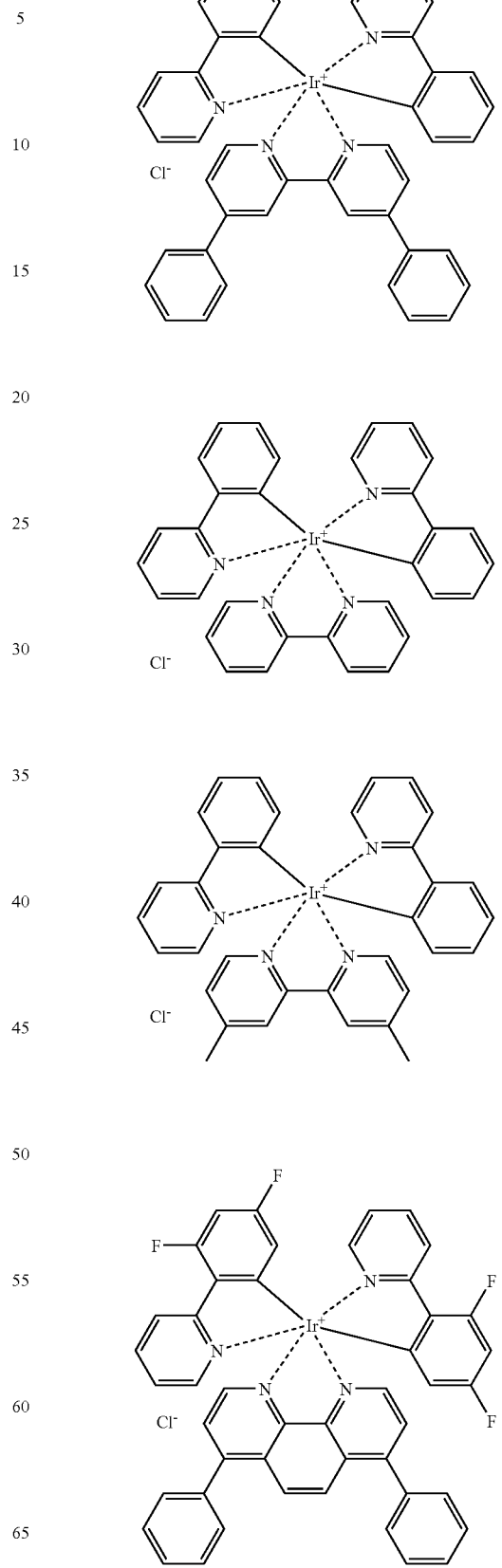

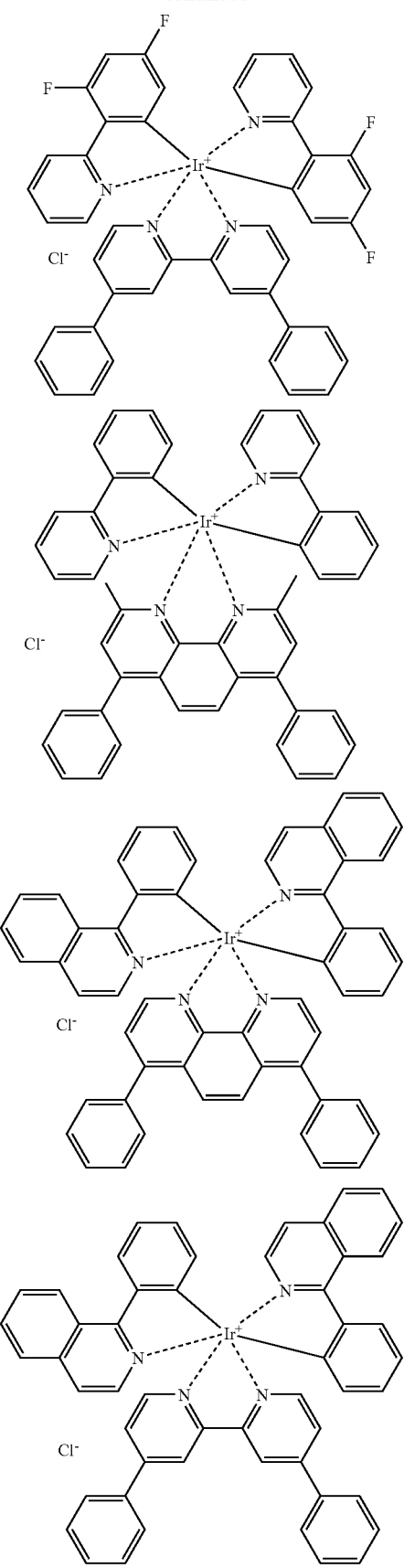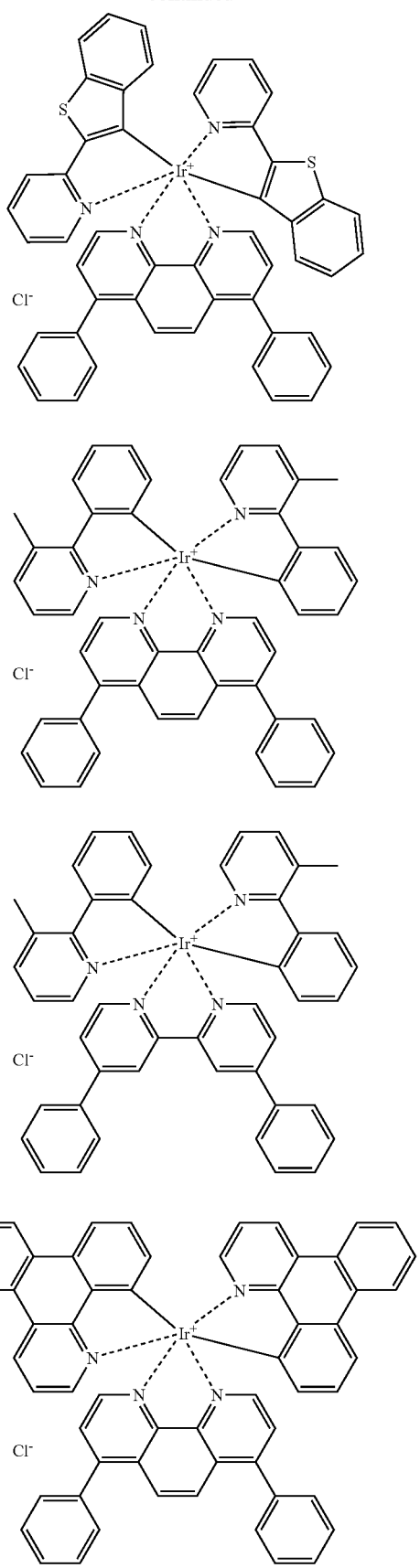

-continued

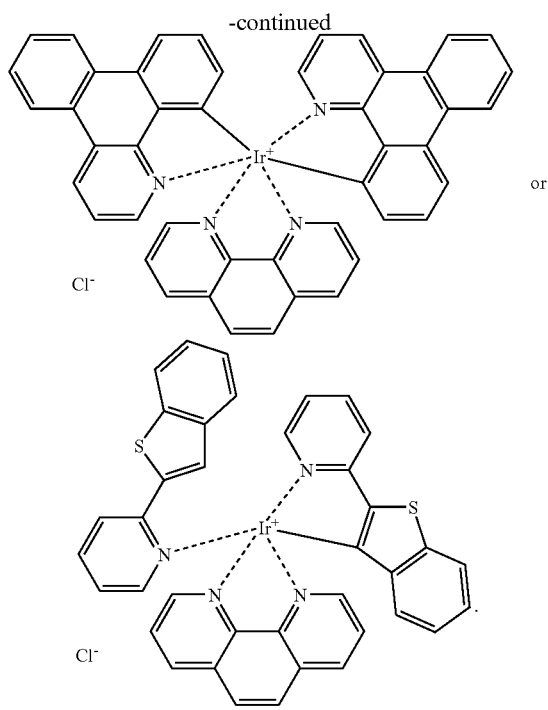

In some embodiments, each metal complex can be compounds 1, 2 or 3. In other embodiments, each metal complex can be compounds 4, 5, 6, 7, 8, 9, 10, 16, 18, 19, 23, 24, 26, 28, 37, 46 or 55. In some other embodiments, each metal complex can be compounds 1, 2, 3, 4, 5, 6, 7, 8, 9, 16, 18, 19, 23, 24, 26, 46 or 55. In still other embodiments, the metal complex is compound 1. In yet other embodiments, the metal complex can be compounds 1, 2, 3, 4, 5, 6, 7, 8, 9, 19, 23, 24, 26, or 46. In still yet other embodiments, the metal complex can be compounds 1, 2, 3, 4, 5, 6, 7, 8, 9 or 46.

III. Method of Staining a Poly(Amino Acid)

In some embodiments, the present invention provides a method of staining a poly(amino acid). The method includes contacting a poly(amino acid) with a metal complex as described above.

A. Method of Use

The present invention utilizes the metal complexes described above to stain poly(amino acids), followed by detection of the stained poly(amino acids) and optionally their quantification or other analysis. By poly(amino acid) is meant any assemblage of multiple amino acids, including homopolymers or heteropolymers of amino acids, that incorporate peptide linkages. Poly(amino acids), as used herein, include peptides and proteins. The poly(amino acids) are stained by combining a sample mixture that is thought to contain poly(amino acids), with a staining mixture that comprises one or more of the metal complexes described above that give a detectable colorimetric or luminescent optical response upon illumination, or that have a detectable intrinsic radioactivity. Additional steps are optionally and independently used in any combination, before, after or concurrently with staining, to provide for separation or purification of the poly(amino acids), for enhancing the detection of the poly (amino acids), for quantification of the poly(amino acids), for identification of a specific poly(amino acid) or group of poly (amino acids) such as by use of an antibody or lectin. The method of the instant invention is both generally and specifically useful in performing many aspects of proteomics, that is, the determination of an accurate profile of protein abundance, structure and activity in a given cell or tissue sample.

Typically, the present invention is utilized to detect poly (amino acids) by combining a sample mixture that is thought to contain a poly(amino acid) with a staining mixture that contains one or more of the metal complexes of the invention to form a combined mixture. The combined mixture is then incubated for a time sufficient for the metal complex in the staining mixture to associate with any poly(amino acid) present in the sample mixture. The resulting stained poly (amino acids) complex are then illuminated at a wavelength where the selected metal complex is excited, and the resulting optical response is detected.

The sample mixture contains or is suspected to contain poly(amino acids). The sample mixture optionally further comprises an aqueous solution, typically prepared with water (e.g. for pure proteins) or aqueous buffer, or is combined with an aqueous solution in the course of labeling. By aqueous solution is meant a solution that is predominantly water and retains the solution characteristics of water. Where the aqueous solution contains solvents in addition to water, water is typically the predominant solvent.

Typically the sample mixture is present on or in a solid or semi-solid matrix. In one embodiment, the solid or semi-solid matrix comprises a membrane, such as a filter membrane. In another embodiment, the solid or semi-solid matrix comprises an electrophoresis medium, such as a polyacrylamide gel, agarose gel, linear polyacrylamide solution, polyvinyl alcohol gel, or capillary electrophoresis buffer. In one embodiment of the invention, the solid or semi-solid matrix comprises a membrane, such as a nitrocellulose or poly(vinylidene difluoride) membrane, wherein the poly(amino acids) are immobilized on the membrane by blotting, spotting, or other method of application. In other embodiments, the solid or semi-solid matrix can be a SDS-PAGE gel.

The poly(amino acids) that are suitable for staining using this method include both synthetic and naturally occurring poly(amino acids), comprising both natural and unnatural amino acids. The poly(amino acids) of the invention include peptides, polypeptides and proteins. Poly(amino acids) that are labeled and analyzed according to the present method optionally incorporate non-peptide regions (covalently or non-covalently) including lipid (lipopeptides and lipoproteins), phosphate (phosphopeptides and phosphoproteins), and/or carbohydrate (glycopeptides and glycoproteins) regions; or incorporate metal chelates or other prosthetic groups or non-standard side chains; or are multi-subunit complexes, or incorporate other organic or biological substances, such as nucleic acids. The poly(amino acids) are optionally relatively homogeneous or heterogeneous mixtures of poly (amino acids). In one aspect of the invention, the poly(amino acids) contain at least one basic amino acid such as lysine, arginine or histidine. In another aspect of the invention the poly(amino acids) are enzymes, antibodies, transcription factors, secreted proteins, structural proteins, nuclear protein, or binding factors, or combinations thereof. In yet another aspect of the invention, the poly(amino acids) comprise the proteome of a cell.

The poly(amino acids) in the sample mixture are optionally covalently or non-covalently bound to a solid or semi-solid surface, such as a glass slide, multi-well plate (such as a 96 well plate), plastic pin, polymeric membrane or bead, or semiconductor material, or they are unbound. The staining of a poly(amino acid) that is bound to an analyte on a solid surface indicates the presence of the analyte as well as that of the poly(amino acid).

The poly(amino acids) are obtained from a variety of sources; such sources including biological fermentation media and automated protein synthesizers, as well as prokaryotic cells, eukaryotic cells, virus particles, tissues, and biological fluids. Suitable biological fluids include, but are not limited to, urine, cerebrospinal fluid, blood, lymph fluids, interstitial fluid, cell extracts, mucus, saliva, sputum, stool, physiological or cell secretions or other similar fluids. In one embodiment, the poly(amino acids) comprise the proteome of an animal cell, typically a mammalian cell.

Depending on the source of the sample mixture, it optionally contains discrete biological ingredients other than the desired poly(amino acids), including poly(amino acids) other than those desired, amino acids, nucleic acids, carbohydrates, and lipids, which may or may not be removed in the course of, prior to, or after staining. In one aspect of the invention, the poly(amino acids) in the sample mixture are separated from each other or from other ingredients in the sample mixture by mobility (e.g. electrophoretic gel or capillary) or by size (e.g. centrifugation, pelleting or density gradient), or by binding affinity (e.g. to a filter membrane or affinity resin) in the course of the method. In another aspect of the invention, the sample mixture thought to contain the poly(amino acids) has undergone separation. In yet another aspect of the invention, the poly(amino acids) are not separated. In one embodiment, the sample mixture is essentially cell-free. In another embodiment, the sample mixture comprises viable cells, non-viable cells, cellular organelles such as nuclei or mitochondria, or a mixture thereof. In another embodiment of the invention, the sample mixture comprises tissues, tissue slices, tissue smears, entire organs, or organisms. In yet another embodiment of the invention, the components of the sample mixture are physically separated before or while it is combined with the staining mixture, including but not limited to separation by flow cytometric, electrophoretic, or microfluidic methods. Where the components of the sample mixture include cells, the cells are optionally separated based on their detectable optical response, which is then correlated to cell viability.

The poly(amino acids) are optionally unmodified, or have been treated with a reagent or molecular composition so as to enhance or decrease the mobility of the poly(amino acid) in an electrophoretic gel. Such reagents may modify poly (amino acids) by complexing with the peptide (typically to decrease migration), by cleaving selected peptide bonds (typically to increase migration of the resulting fragments), by changing the relative charge on the protein (such as by acylation, phosphorylation or dephosphorylation) or by covalent coupling of a constituent such as occurs during glycosylation. The presence or interaction of such a reagent in the sample mixture is detected by the change in electrophoretic mobility of the treated poly(amino acids), relative to untreated poly(amino acids) having the same original composition, so that the distribution of the poly(amino acid) indicates the presence of another analyte.

Typically the poly(amino acids) in the sample mixture have a molecular weight greater than about 500 Daltons. More typically the poly(amino acids) are more than 800 Daltons. The poly(amino acids) present optionally have essentially the same molecular weight or fall within a range of molecular weights. In one embodiment of the invention, the poly(amino acids) present are a mixture of poly(amino acids) of different molecular weights that are used as molecular weight standards. Typically, such a mixture contains equal mass quantities of myosin, β-galactosidase, phosphorylase B, bovine serum albumin, ovalbumin, carbonic anhydrase, trypsin inhibitor, lysozyme and aprotinin. The metal complexes of the present invention also stain low molecular weight peptides, polypeptides and proteins, such as insulin, aprotinin, or neuropeptides.

In some embodiments of the invention, separated poly (amino acids) in electrophoretic gels are post-stained using the staining mixture, or are transferred to a filter membrane or blot or other solid or semi-solid matrix before being combined with the staining mixture. The present method is effective for both denaturing and non-denaturing gels. Denaturing gels optionally include a detergent such as SDS (sodium dodecyl sulfate) or other alkyl sulfate (e.g. 0.05%-0.1% SDS). Typically, polyacrylamide or agarose gels are used for electrophoresis. Commonly used polyacrylamide gels include but are not limited to Tris-glycine, Tris-tricine, mini- or full-sized gels, generally possessing a stacking gel. Agarose gels include modified agaroses. Alternatively, the gel is an iso-electric focusing gel or strip. In addition to polyacrylamide and agarose gels, suitable electrophoresis gels are optionally prepared using other polymers, such as HYDROLINK. Alternatively, the electrophoretic gel is a gradient gel. Useful electrophoretic gels for the present invention are either prepared according to standard procedures or are purchased commercially.

In another embodiment of the invention, the present method is used to detect poly(amino acids) present in a two-dimensional electrophoretic gel. In another embodiment of the invention, the electrophoretic gel is used for gel-mobility-shift analysis, where a polyacrylamide or agarose gel is cast and run in a buffer optimized to preserve the specific protein/nucleic acid interaction of interest. In both embodiments, the staining mixture is optionally combined with the sample mixture at any stage in the electrophoresis procedure, but the dyes are preferably used following electrophoretic separation as a post-stain.

Where the sample mixture is on or in an electrophoretic gel or a blot membrane, the poly(amino acids) of the sample mixture are typically present at a concentration of 0.1 ng/band to 4 µg/band.

In yet another embodiment of the invention, the present method is used to detect poly(amino acids) that are themselves associated with a target of interest. For example, a target molecule is labeled with biotin, which is then labeled with streptavidin using standard immunological methods. The streptavidin is then stained using a metal complex of the invention. Luminescent detection of the streptavidin results in detection and/or localization of the target of interest. Similarly, a target can be labeled with a polypeptide, which is then directly detected using a metal complex of the invention.

In some embodiments, the method of the present invention is performed in the absence of de-staining the poly(amino acid). In other embodiments, the method is performed in the absence of fixing the poly(amino acid).

Fixing or fixation is a treatment that can be applied to electrophoretically separated protein gels prior to application of staining solution. Fixing involves soaking the gel in a aqueous fixing solution that contains an acidic component and can additionally contain a water-miscible organic solvent. Examples of the acidic component include acetic acid, trichloroacetic acid and phosphoric acid. Acid is typically present at a concentration of 0.1% to 20%. Examples of the water-miscible organic solvent component include methanol, ethanol and isopropanol. Water miscible organic solvent, when present, is typically present at a concentration of 5% to 60%. The fixing step immobilizes proteins within the gel and prevents them from diffusing out of the gel during subsequent staining steps. The fixing step can also serve to wash out substances present in the gel that would otherwise interfere with subsequent staining. Such substances include detergents, buffers and salts. The fixing step can be a single step or multiple steps involving changes of one or more fixing solutions.

If the staining solution contains an acidic component and a miscible organic solvent component (as does the staining solution of the instant invention), it can be possible to stain without a fixing step, as the staining solution contains the components required to immobilize proteins within the gel. This is possible if substances in the gel such as detergents, buffers and salts do not interfere with staining.

Destaining is a treatment that can be applied to electrophoretically separated protein gels subsequent to application of staining solution. The destaining solution can consist of water alone or comprise an aqueous solution containing any combination of one or more of the following: water-miscible organic solvents, acidic components, inorganic salts, buffers, surfactants. The destaining step serves to wash out or lower the concentration of stain within the gel that is not associated with protein. This lowers background photoluminescence and allows gel separated protein to be better detected, visualized and quantified.

B. Staining Mixture

In order to effect poly(amino acid) staining, the sample mixture is combined with a staining mixture. A staining mixture is typically prepared by dissolving a selected metal complex in a solvent, such as water, DMSO, DMF or methanol, usually to a metal complex concentration of 0.1-20 µM. The staining mixture can be prepared from a more concentrated stock solution containing the metal complex. The stock solution is generally diluted with an aqueous solution according to the assay being performed. Staining solutions, or the stock solutions from which they are prepared can be stored for months. For staining poly(amino acids) on gels or membranes, the metal complex is diluted into a solution that comprises water, and optionally further comprises additional formulation components, such as acids, buffering agents, inorganic salts, polar organic solvents, antioxidants, surfactants and ion chelators. In some instances, the staining solution can be reused.

Although the instant method of staining is most useful when used in conjunction with detection of luminescence, some metal complexes used for the invention have calorimetric absorbance and can be detected by their visible color absorbance. For luminescence detection, the staining mixture comprises the metal complex at a typical concentration of greater than 0.10 µM and less than 10 µM; preferably greater than about 0.50 µM and less than or equal to about 5 µM; more preferably 1-3 µM. Where the staining method of the invention is being utilized to determine cell viability, the metal complex is typically present in a concentration of about 1-5 µM, preferably about 3 µM. In one embodiment, the metal complex is present at a concentration of about 1.5 µM. In another embodiment, the metal complex is present at a concentration of about 5 µM.

Transition metal complexes can have luminescence lifetimes that are longer than those of other luminescent compounds that can be present in the sample or on the support that has been stained. This property can be exploited for additional sensitivity or discrimination by using time-resolved methods of luminescence detection.

A particular metal complex is generally selected for a particular assay using one or more of the following criteria: sensitivity to poly(amino acids) in general or to a specific class thereof, dynamic range, photostability, staining time, and insensitivity to the presence of nucleic acids. Preferably, the metal complexes of the present invention are capable of detecting 1-2 ng or less of poly(amino acid) per spot or band in electrophoretic gels.

The metal complexes of the invention readily stain proteins at a wide variety of pH values. Typically the staining mixture has a pH of about 1 to about 10, more typically the staining mixture has a pH of about 1 to about 5. The pH of the staining mixture can be controlled by the selection of appropriate acidic components or buffering agents.

In some embodiments, the metal complex is in an acidic solution. In some embodiments, the acidic solution is a solution of citric, oxalic, formic, acetic, trichloroacetic, sulfosalicylic, or benzenesulfonic acid. In other embodiments, the acidic solution is a solution of phosphoric acid.

Where the presence of an acidic component in the staining mixture is desirable, any acidic component that is compatible with poly(amino acids) is a suitable acidic component. Typical suitable acidic components include without limitation acetic acid, trichloroacetic acid, trifluoroacetic acid, perchloric acid, phosphoric acid, sulfuric acid, citric, oxalic, formic, trichloroacetic sulfosalicylic, or benzesulfonic acid. The acidic component is typically present at a concentration of 0.1%-20% (v/v). Where the acidic component is acetic acid, it is typically present at a concentration of 1%-10% (v/v). Where the acidic component is trichloroacetic acid, it is typically present at a concentration of 7%-30% (v/v), preferably 10%-20% (v/v), more preferably 12%-13% (v/v). Where the acidic component is perchloric acid, it is typically present at a concentration of 2-5% (v/v). Where the acidic component is phosphoric acid, it is typically present at a concentration of 0.1%-5% (v/v).

The pH of the staining mixture is optionally modified by the inclusion of a buffering agent in addition to or in place of an acidic component. Any buffering agent that is compatible with the poly(amino acids) in the sample is suitable for inclusion in the staining mixture.

In one embodiment, the buffering agent is one of the so-called "Good" buffers. "Good" buffers include BES (N,N-bis[2-hydroxyethyl]-2-aminoethanesulfonic acid; 2-[bis(2-hydroxyethyl)amino]ethanesulfonic acid); BICINE (N,N-bis[2-hydroxyethyl]glycine), CAPS (3-[cyclohexylamino]-1-propanesulfonic acid), EPPS(N-[2-hydroxyethyl]piperazine-N'-[3-propanesulfonic acid]), HEPES ((N-[2-hydroxyethyl]piperazine-N'-[2-ethanesulfonic acid]), MES (2-[N-morpholino]ethanesulfonic acid), MOPS (3-[N-morpholino]propanesulfonic acid), PIPES (piperazine-N,N'-bis[2-ethanesulfonic acid]; 1,4-piperazinediethanesulfonic acid), TAPS(N-tris[hydroxymethyl]methyl-3-aminopropanesulfonic acid; ([2-hydroxy-1,1-bis(hydroxymethyl)ethyl]amino-1-propanesulfonic acid), TES (N-tris[hydroxymethyl]methyl-2-aminoethanesulfonic acid; 2-([2-hydroxy-1,1-bis(hydroxymethyl)ethyl]amino)ethanesulfonic acid), or TRICINE (N-tris[hydroxymethyl]methylglycine; N-[2-hydroxy-1,1-bis(hydroxymethyl)ethyl]glycine).

Other useful buffering agents include salts of formate, citrate, acetate, 2-(N-morpholino) ethanesulfonic acid, imidazole, N-2-hydroxyethyl-piperazine-N'-2-ethanesulfonic acid, Tris(hydroxymethyl)aminomethane acetate, or Tris(hydroxymethyl)aminomethane hydrochloride. In a preferred embodiment, the buffering agent is sodium acetate. The buffering agent is typically present in the staining mixture at a concentration of 20 mM to 500 mM, in another aspect at a concentration of 50 mM to 200 mM, and in another aspect at a concentration of about 100 mM.

Any inorganic salt that is adequately soluble in the formulation itself may be used in the staining formulations. Advantageous inorganic salts produce staining formulations that exhibit low background signals in stained gels. Inorganic salts useful in the present invention include, but are not limited to, sodium chloride, potassium chloride, ammonium sulfate, magnesium chloride, zinc chloride, sodium acetate, magnesium sulfate and magnesium glucuronate. Inorganic salts can be present in the staining mixture at a concentration of 1-50% (w/v).

In some embodiments, the staining mixture comprises a polar organic solvent. Polar solvents useful in the methods of the present invention include, but are not limited to, water, methanol, ethanol, propanol, isopropanol, butanol, sec-butanol, isobutanol, tert-butanol, ethylene glycol, propylene glycol, glycerol, dimethyl sulfoxide, dimethyl formamide, sulfolane, methyl formamide, dimethylacetamide, methylacetamide, formamide, methyl pyrrolidone, pyrrolidone, dimethylimidazolinone, acetonitrile, ethoxyethanol, methoxyethanol, methylpyrrolidone, tetrahydrofuran, dioxane and diglyme. When the polar solvent is an alcohol, the alcohol can have 1-6 carbon atoms, or can be a diol or triol having 2-6 carbon atoms. The polar solvent, when present, is typically included in the staining mixture at a concentration of 5-50% (v/v).

Staining of poly(amino acids) is optionally enhanced by the addition of an antioxidant or a transition metal ion chelator. Selected embodiments of antioxidants include glucuronic acid, ascorbic acid and citric acid. Selected embodiments of transition metal ion chelators include ethylenediamine diacetic acid, ethylenediamine tetraacetic acid (EDTA), ethylene glycol-bis-(β-aminoethyl ether)tetraacetic acid (EGTA), citric acid, 1,2-bis-(2-aminophenoxyethane)-N,N,N',N'-tetraacetic acid (BAPTA), 2-carboxymethoxy-aniline-N,N-diacetic acid (APTRA), and various crown ethers. Citric acid may act as both an antioxidant and a chelating group, and is a particularly useful additive to the staining mixture.

Staining of poly(amino acids) can be enhanced by the presence of a surfactant. Selected embodiments of surfactants include any of the Pluronics, Triton X-100 and Tween 20. Surfactants can be used individually or as mixtures of two or more surfactants. Surfactant can be present at a total concentration of 0.002% to 10% (w/v), more typically at a concentration of 0.01% to 1% (w/v). A surfactant can be present in the concentrated stock solution of the staining reagent. A preferred surfactant additive is Pluronic F127. One of skill in the art will appreciate that other surfactants are useful in the present invention.

When the metal complexes of the invention are prepared, the staining mixture stains poly(amino acids) in polyacrylamide gels with greatly reduced background staining. A low background level of luminescence is particularly important for quantitative measurements of poly(amino acid) bands, as any destaining procedure would invariably remove some staining from the poly(amino acid) band.

C. Combined Mixture

The staining mixture is combined with the sample mixture in such a way as to facilitate contact between the metal complex and any poly(amino acids) present in the combined mixture. Poly(amino acids) that have been separated by gel electrophoresis can be stained by immersion of the gel in the staining mixture.

Destaining of stained gels is typically not necessary for luminescent detection of proteins using the metal complexes of the invention. The persistence and stability of staining is such that stained gels can be photographed weeks after staining without significant loss of signal.

Destaining can be performed to decrease background staining or otherwise increase detection sensitivity. Destaining can be performed by immersion of the gel in water, or in a mixture of water and any of the following components in combination or individually: polar solvent, acid, buffer, salt or surfactant.

Electrophoretic gels stained according to the method of the invention can subsequently be dried onto filter paper or between plastic sheets (e.g. cellophane), using standard procedures.

D. Additional Reagents

The method of the present invention optionally further comprises one or more additional reagents that are simultaneously or sequentially combined with the sample mixture, the staining mixture, or the combined mixture. An additional reagent is optionally a detection reagent that colocalizes with poly(amino acids) in general or with specific poly(amino acids) to enhance the detection thereof by the method of the present invention. Alternatively, the additional reagent is useful for identification of other components in the sample mixture, such as a nucleic acid stain, or a stain for lipids, carbohydrates, specific protein classes or specific protein modifications such as phosphorylation or glycosylation. Or, the additional reagent is a detection reagent designed to interact with a specific portion of the sample mixture, so as to probe for a specific component of the sample mixture, where spatial coincidence of the metal complex and the detection reagent indicates that the additional reagent is also associated with the poly(amino acids).

The additional reagent also incorporates a means for producing a detectable response. A detectable response means a change in, or occurrence of, a parameter in a test system that is capable of being perceived, either by direct observation or instrumentally. Such detectable responses include the change in, or appearance of, color, fluorescence, reflectance, pH, chemiluminescence, infrared spectra, magnetic properties, radioactivity, light scattering, x-ray scattering, or the precipitation of an electron-rich substrate. Appropriate labels to provide a detectable response include, but are not limited to, a visible or fluorescent dye, a chemiluminescent reagent, an enzyme substrate that produces a visible or fluorescent precipitate upon enzyme action (for example, the action of horseradish peroxidase upon diaminobenzidine, or enzyme action on a labeled tyramide), visible or fluorescent labeled microparticles, a metal such as colloidal gold, or a silver-containing reagent, or a signal that is released by the action of light upon the reagent (e.g. a caged fluorophore that is activated by photolysis, or the action of light upon diaminobenzidine). The detectable label of the additional reagent is detected simultaneously or sequentially with the optical signal of the complexes of the present invention.

In one embodiment of the invention, one or more additional dyes or photoluminescent substances, including preferred embodiments described above, are the additional reagent(s). The individual dyes or photoluminescent substances may be selected to exhibit overlapping spectral characteristics, such that energy transfer occurs between substances associated with the poly(amino acids), resulting in labeled poly(amino acids) that exhibit an extended Stokes shift. Alternatively, additional dye(s) colocalize with the metal complex such that the labeling of some or all poly(amino acids) exhibits quenching. Alternatively, the additional reagent is another protein stain (such as CBB or silver stain) such that labeling of the poly(amino acids) is enhanced by the colocalization of staining.

Other useful additional reagents are fluorescent nucleic acid stains. A variety of appropriate nucleic acid stains are known in the art, including but not limited to, thiazole orange, ethidium homodimer, ethidium bromide, propidium iodide, HOECHST 33258, and DAPI. Additional useful nucleic acid stains are described in the international applications WO 93/06482, DIMERS OF UNSYMMETRICAL CYANINE DYES (published Apr. 1, 1993) or WO 94/24213, CYCLIC SUBSTITUTED UNSYMMETRICAL CYANINE DYES (published Oct. 27, 1994); U.S. Pat. No. 5,321,130 to Yue et al., 1994; or U.S. Pat. No. 5,410,030 DIMERS OF UNSYMMETRICAL CYANINE DYES CONTAINING PYRIDINIUM MOIETIES to Yue et al., 1995. The use of an appropriate nucleic acid stain in conjunction with the dyes of the present invention can be selected to allow simultaneous or sequential observation of poly(amino acids) and nucleic acids such as DNA and RNA.

The additional reagent may be used in conjunction with enzyme conjugates to localize the detectable response of the reagent. Enzyme-mediated techniques take advantage of the attraction between specific binding pairs to detect a variety of analytes. In general, an enzyme-mediated technique uses an enzyme attached to one member of a specific binding pair or series of specific binding pairs as a reagent to detect the complementary member of the pair or series of pairs. In the simplest case, only the members of one specific binding pair are used. One member of the specific binding pair is the analyte, i.e. the substance of analytical interest. An enzyme is attached to the other (complementary) member of the pair, forming a complementary conjugate. Alternatively, multiple specific binding pairs may be sequentially linked to the analyte, the complementary conjugate, or to both, resulting in a series of specific binding pairs interposed between the analyte and the detectable enzyme of the complementary conjugate incorporated in the specific binding complex.

In another embodiment of the invention, an electrophoresis gel stained according to the method of the invention may be imaged, and subsequently incubated with a detection reagent that is a primary antibody. The resulting immunolabeled gel is then restained according to the method of the invention. The metal complex of the invention will associate with and stain the primary antibody just as it stains other poly(amino acids), and thereby increase the overall staining of the gel. In this embodiment, even an unlabeled antibody could be used for immunolabeling, as the presence of the label does not appreciably effect staining by the instant complexes. This methodology is particularly useful for high-throughput image analysis, permitting automated workstations to rapidly screen stained gels for spots that increase in intensity upon labeling and restaining. The staining of other poly(amino acid) labels, for example actin that is used to identify actin-binding proteins, is readily accomplished in the same manner.

E. Illumination and Observation

Where the metal complex of the invention incorporates a radioactive transition metal ion (such as an α-, β-, or γ-emitter), the presence and location of the metal complex in the combined mixture is optionally detected by radiography. Typically, intrinsic radioactivity is detected using film, phosphor storage plates, or microscanner array detectors.

The metal complex is most typically detected by its intrinsic luminescence. After addition of the metal complex to the sample mixture, the sample mixture is illuminated by a light source capable of exciting the stained sample mixture. Typically, the sample mixture is excited by a light source capable of producing light at or near a wavelength of peak absorption of the metal complex, such as an ultraviolet or visible wavelength emission lamp, a laser, an arc lamp, a fluorescent bulb, or even an incandescent bulb. Preferably the sample mixture is excited with a wavelength within 20 nm of the maximum absorption of the metal complex. Although excitation by a source more appropriate to the maximum absorption band of the metal complex may result in higher sensitivity, the equipment commonly available for excitation of fluorescent samples can be used to excite the stains of the present invention. Selected equipment that is useful for illuminating the metal complex includes, but is not limited to, ultraviolet trans-illuminators, ultraviolet epi-illuminators, hand-held ultraviolet lamps, mercury arc lamps, xenon lamps, argon-ion lasers, diode lasers, and Nd-YAG lasers. These illumination sources are optionally integrated into laser scanners, fluorescence microplate readers, standard or mini fluorometers, microscopes, flow cytometers, gel readers, or chromatographic detectors.

As the metal complexes of the invention possess long-lifetime luminescence, observation of luminescence may occur at greater than about 100 nanoseconds after illumination, even up to greater than 10 microseconds after illumination. Utilizing this 'time-resolved' luminescence results in the exclusion of almost all of the sources of background fluorescence, which is typically short-lived. This property is particularly useful where samples are intrinsically fluorescent, have fluorescent impurities, or in combination with other detection reagents that give prompt fluorescence.

In another embodiment of the invention, the presence or amount of poly(amino acids) in the sample mixture is detected by measuring the polarization of the luminescence of the metal complexes of the invention. The technique of fluorescence polarization involves exciting a fluorescent- or luminescent-labeled sample mixture with polarized light, and measuring the polarization of the resulting fluorescence. Where the labeled molecule is large and rotates slowly (such as stained poly(amino acids)), the change in polarization between the excitation light and the resulting fluorescence is very small. Where the labeled molecule is small and rotates rapidly (such as the metal complex in the absence of poly(amino acids)), the change in polarization is large. Fluorescence polarization assays typically use samples that are homogenous solutions.

The detectable optical response of the metal complex in response to illumination is detected qualitatively, or optionally quantitatively. The detectable optical response of the metal complex is typically a long-lifetime luminescence response.

The optical response is typically detected by means that include visual inspection, CCD cameras, video cameras, photographic film, or the use of currently used instrumentation such as laser scanning devices, fluorometers, photodiodes, quantum counters, epifluorescence microscopes, scanning microscopes, flow cytometers, fluorescence microplate readers, or by means for amplifying the signal such as photomultiplier tubes. When recording the optical response of electrophoretic gels, the use of a film such as POLAROID film results in enhanced sensitivity of signal versus purely visual observation. The sensitivity of detection is improved by use of techniques that permit separation of the poly(amino acids) on very thin gels or in microtube capillaries. The detection limits may also be improved if the medium is illuminated by a stronger light such as a laser, detected with a more sensitive detector, or background signals are reduced via detection of delayed luminescence. The high Stokes shifts of the metal complexes of the present invention result in an excellent signal-to-noise ratio by decreasing the contribution of scattered light and endogenous fluorescence to the background.

The presence of luminescence is optionally used to identify the presence of poly(amino acids) in the test sample. Alternatively, the detectable optical response is quantified and used to measure the concentration of the poly(amino acid) in the test sample mixture. Quantification is typically performed by comparison of the optical response to a prepared standard or to a calibration curve. Typically, the measured optical response is compared with that obtained from a standard dilution of a known concentration of a poly(amino acid) or poly(amino acid) mixture in an electrophoretic gel, or on a membrane. Generally a standard curve must be prepared whenever an accurate measurement is desired. Alternatively, the standard curve is generated by comparison with a reference dye or dyed particle that has been standardized versus the metal complex-stained poly(amino acids).

Stained electrophoretic gels are used to analyze the composition of complex sample mixtures and additionally to determine the relative amount of a particular poly(amino acid) in such mixtures. Stained gels are also used to estimate the purity of isolated proteins and to determine the degree of proteolytic degradation of poly(amino acids) in the sample mixture. In addition, electrophoretic mobility is optionally used to provide a measure of the size of uncharacterized poly(amino acids) and to analyze subunit composition for multi-subunit proteins, as well as to determine the stoichiometry for subunits bound in such proteins. In the case of isoelectric focusing electrophoresis (IEF), electrophoretic mobility is used to provide a measure of the net molecular charge possessed by the poly(amino acid).

The use of the complexes of the invention provides higher sensitivity poly(amino acid) detection than other comparable electrophoresis gel stains when used with ultraviolet excitation. In one aspect of the invention, the instant method is utilized with automated electrophoresis methods. Using the instant method, the bright luminescence of even small amounts of poly(amino acids) permits their detection by automated imaging systems. Furthermore, unlike many electrophoretic gel stains, the instant method incorporates 'endpoint staining'. That is, while an electrophoretic gel may be compromised by silver staining beyond the optimum end point, gels stained using the instant method do not suffer from prolonged staining, and do not require destaining, further simplifying the use of automated staining systems. The sensitivity and ultraviolet excitation of the instant metal complexes facilitate the accurate localization of poly(amino acid) bands or spots by automatic systems, permitting their subsequent transfer and/or analysis.

In one aspect of the invention, the localization of poly (amino acid) bands or spots further comprises the physical removal of the bands or spots, followed by separation of the poly(amino acids) from the electrophoretic matrix. In another aspect of the invention, the localization of poly(amino acid) bands or spots further comprises ionization of the poly(amino acids) and characterization by mass spectroscopy, or transfer and subsequent analysis of the poly(amino acids) by Edman sequencing.

IV. Kits

In some embodiments, the present invention provides a kit comprising a stock solution of a metal complex, a polar organic solvent at a concentration from about 5 to about 50%, an acidic component at a concentration from about 1% to about 20%, an inorganic salt that is present at a concentration of about 1% to about 50%, or both and a surfactant at a total concentration of 0.002% to 10%, more typically at a concentration of 0.01 to 1%. The metal complexes of the present invention will have at least one transition metal ion, and a plurality of donor ligands each fully coordinated to the transition metal ion, wherein each donor ligand is a nitrogen donor ligand or a cyclometalated donor ligand. Each donor ligand can be the same or different. Nitrogen donor ligands will contain heteroaryl ring systems having from 10 to 40 ring atoms, where from 2 to 8 ring atoms are N, O, S, or combinations thereof, such that at least two ring atoms are N, wherein each nitrogen donor ligand is substituted with from 0 to 4 $R^1$ groups. Cyclometalated donor ligands will likewise contain heteroaryl ring systems having from 10 to 40 ring atoms, where from 1 to 4 ring atoms are N, O, S or combinations thereof, such that at least one ring atom is N, wherein each cyclometalated donor ligand is substituted with from 0 to 4 $R^1$ groups. The $R^1$ groups are $C_{1-6}$ alkyl, $C_{2-6}$ alkenyl, $C_{2-6}$ alkynyl, $C_{1-6}$ alkoxy, halogen, $C_{1-6}$ haloalkyl, —$OR^2$, —$NR^2R^3$, —CN, —$C(O)R^2$, —$C(O)OR^2$, —$OC(O)R^2$, —$C(O)NR^2R^3$, —$N(R^2)C(O)R^3$, —$OC(O)NR^2R^3$, —$N(R^2)C(O)OR^3$, —$NR^2C(O)NR^3R^4$, —$NR^2C(S)NR^3R^4$, —$NO_2$, =O, aryl, heteroaryl, cycloalkyl or heterocycloalkyl. When two or more $R^1$ groups are present on a single donor ligand, they can be the same or different. The $R^2$, $R^3$ and $R^4$ groups are H or $C_{1-12}$ alkyl. Each of the $R^2$, $R^3$ and $R^4$ groups can be the same or different. The metal complex of the present invention is neutral or cationic in overall electronic charge and is present in a concentration from about 0.10 µM to about 10 µM. The kit of the present invention optionally further comprises buffering agents, antioxidants, metal chelators, surfactants or additional detection reagents in the same or different solutions.

Kits comprising the metal complexes of the present invention are also useful. The kits can comprise the metal complexes in dry, powder form, or as a solution. The kits can also include instructions for the use of the metal complex to stain or detect poly(amino acids), as well as poly(amino acid) standards and other components (such as buffers or wash solutions). In one embodiment, the kit of the invention comprises an aqueous stock solution of a metal complex of the invention and one or more additional kit components.

The additional kit components optionally include acids, buffering agents, inorganic salts, polar solvents, antioxidants, or metal chelators. The additional kit components are present as pure compositions, or as aqueous solutions that incorporate one or more additional kit components. Any or all of the kit components optionally further comprise buffers. Where the kit component is an acid, it is optionally phosphoric acid, acetic acid, citric acid or trichloroacetic acid. Where the additional kit component is a polar solvent, it is typically a lower alcohol such as methanol or ethanol. In some embodiments, the additional kit component can be an inorganic salt as described above. The kits of the present invention can also comprise a detection device to detect the poly(amino acids) stained with the metal complexes of the present invention.

V. Examples

Example 1

Preparation and Characterization of Compound 1

Preparation of bis(2-phenylpyridine)(4,7-diphenyl[1, 10]phenanthroline)iridium chloride

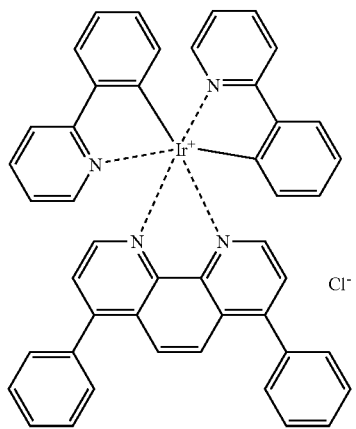

10 mg (9.3 µmol) dichlorotetrakis(2-(2-pyridinyl)phenyl) diiridium and 8.1 mg (24 µmol) bathophenanthroline were dissolved in dichloromethane and stirred under nitrogen for 6 h. The solvent was removed under vacuum and the residue was washed with diethyl ether. This yielded 11.4 mg of light brown crystalline material (71% yield). The expected monoisotopic mass of the molecular ion is 833.2, the measured mass (major peak) is 833.7.

Example 2

Preparation of Compound 2

Step 1—preparation of dichlorotetrakis(benzo[h]quinoline)diiridium

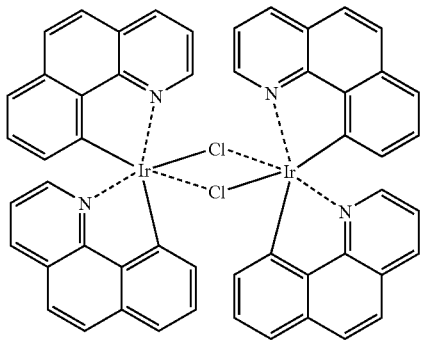

75 mg $IrCl_3.H_2O$ and 186 mg benzo[h]quinoline were dissolved in 4.5 ml ethoxyethanol, 1.5 ml water and refluxed for 24 h. The precipitated solid was collected by filtration and washed with ethanol and acetone. This material was dissolved in 11 ml dichloromethane and precipitated by the addition of 3.75 ml toluene and 1.5 ml hexane. The precipitated material was collected by filtration and vacuum dried. Yield was 51%.

Step 2—preparation of Compound 2 [bis(benzo[h]quinoline)(4,7-diphenyl[1,10]phenanthroline)iridium hexachlorophosphate]

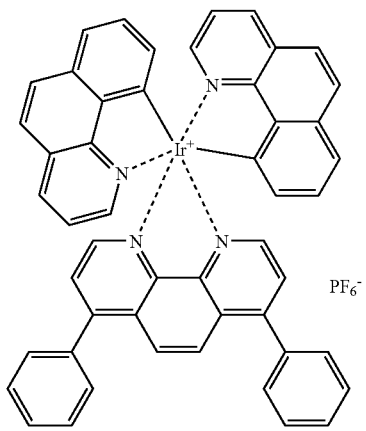

12 mg of dichlorotetrakis(benzo[h]quinoline)diiridium and 8 mg of 4,7-diphenyl[1,10]phenanthroline were added to 1 ml dichloromethane and stirred 18 h at room temperature. The material was dried down and dissolved in methanol Compound 2 was precipitated as a hexafluorophosphate salt by the addition of a saturated solution of $KPF_6$. The precipitated material was collected by filtration and vacuum dried. Yield was 36%. The expected monoisotopic mass of the molecular ion is 881.2, the measured mass (major peak) is 881.7.

Example 3

Preparation of Compound 3

Step 1—preparation of dichlorotetrakis(2-phenylbenzothiazole)diiridium

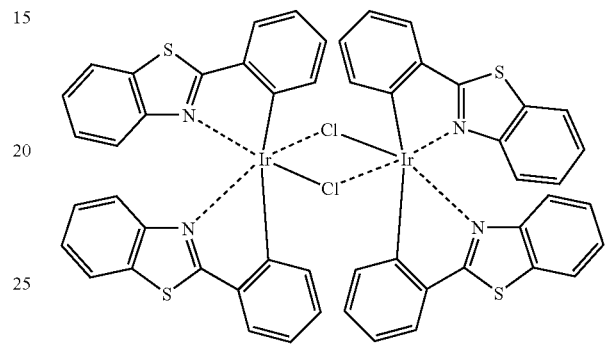

75 mg $IrCl_3.H_2O$ and 190 mg 2-benzothiazole were dissolved in 4.5 ml ethoxyethanol, 1.5 ml water and refluxed for 24 h. The precipitated solid was collected by filtration, washed with ethanol and acetone and extracted with hot chloroform. This material was dissolved in 11 ml dichloromethane and precipitated by the addition of 3.75 ml toluene and 1.5 ml hexane. The material was collected by filtration and vacuum dried. Yield was 83%.

Step 2—preparation of Compound 3 [bis(2-phenylbenzothiazole)(4,7-diphenyl[1,10]phenanthroline) iridium hexachlorophosphate]

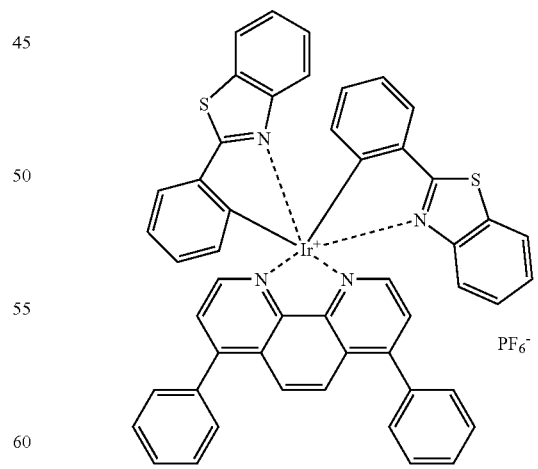

14 mg of dichlorotetrakis(2-phenylbenzothiazole)diiridium and 8 mg of 4,7-diphenyl[1,10]phenanthroline were added to 1 ml dichloromethane and stirred 18 h at room temperature. The material was dried down and dissolved in methanol Compound 2 was precipitated as a hexafluorophosphate salt by the addition of a saturated solution of KPF$_6$. The precipitated material was collected by filtration and vacuum dried. Yield was 11%. The expected monoisotopic mass of the molecular ion is 945.2, the measured mass (major peak) is 945.7.

Example 4

Preparation of Compounds 4-10, 16, 18, 19, 23, 24, 26, 28, 37, 46 and 55

Compounds 4-10, 16, 18, 19, 23, 24, 26, 28, 37, 46 and 55 were prepared according to methods known in the art (Sprouse, S. et al. J. Am. Chem. Soc. 1984, 106, 6647-6653; Ohsawa, Y. et al. J. Phys. Chem. 1987, 91, 1047-1054). Cyclometalated dichloro bridged dimeric precursors were prepared by refluxing 0.9 mmol of cyclometalated donor ligand with 0.24 mmol of IrCl$_3$.H$_2$O in 4.5 ml ethoxyethanol and 1.5 ml water for 16 hr. Volume was reduced under vacuum and the material was collected by filtration. Yield was typically in excess of 85% following washing with diethyl ether and ethanol. The compounds described were prepared by mixing 20 μmol of dichloro bridged dimeric precursor with 50 μmol of nitrogen donor ligand in 2 ml of methylene chloride and stirring under argon for 3 h. The compounds were purified by silica gel chromatography (chloroform:ethanol 9:1).

Identity of each synthesized compound was verified by matrix free laser desorption ionization mass spectrometry (below):

| Compound | Expected monoisotopic mass of molecular ion | Measured mass (major peak) |
|---|---|---|
| 4 | 1081.1 | 1081.1 |
| 5 | 905.2 | 905.9 |
| 6 | 933.3 | 933.1 |
| 7 | 945.2 | 945.1 |
| 8 | 861.3 | 861.1 |
| 9 | 981.3 | 981.4 |
| 10 | 681.2 | 681.3 |
| 16 | 793.1 | 793.0 |
| 18 | 829.2 | 829.1 |
| 19 | 809.2 | 809.8 |
| 23 | 881.2 | 881.9 |
| 24 | 909.3 | 909.3 |
| 26 | 837.3 | 837.1 |
| 28 | 657.2 | 657.6 |
| 37 | 685.2 | 685.6 |
| 46 | 861.3 | 861.1 |
| 55 | 743.2 | 743.2 |

Example 5

Staining a Poly(Amino Acid)

The described compound is used to fluorescently stain proteins separated by SDS-polyacrylamide gel electrophoresis (SDS-PAGE). A simple and rapid staining procedure is used and the stained gels are imaged by transillumination with UV light and photography through a suitable filter. Protein-associated luminescence is higher than with comparable methods and detection limits of 1 ng of protein or less are obtainable with relatively brief exposure times.

Stock solutions of the materials were prepared by dissolving in dimethyl sulfoxide to a concentration of 10 mg/ml (Compound 1) or 7.5 mg/ml (Compounds 2 and 3) and subsequently diluting 50-fold into 10% (w/v) aqueous Pluronic F127.

Figure 3:
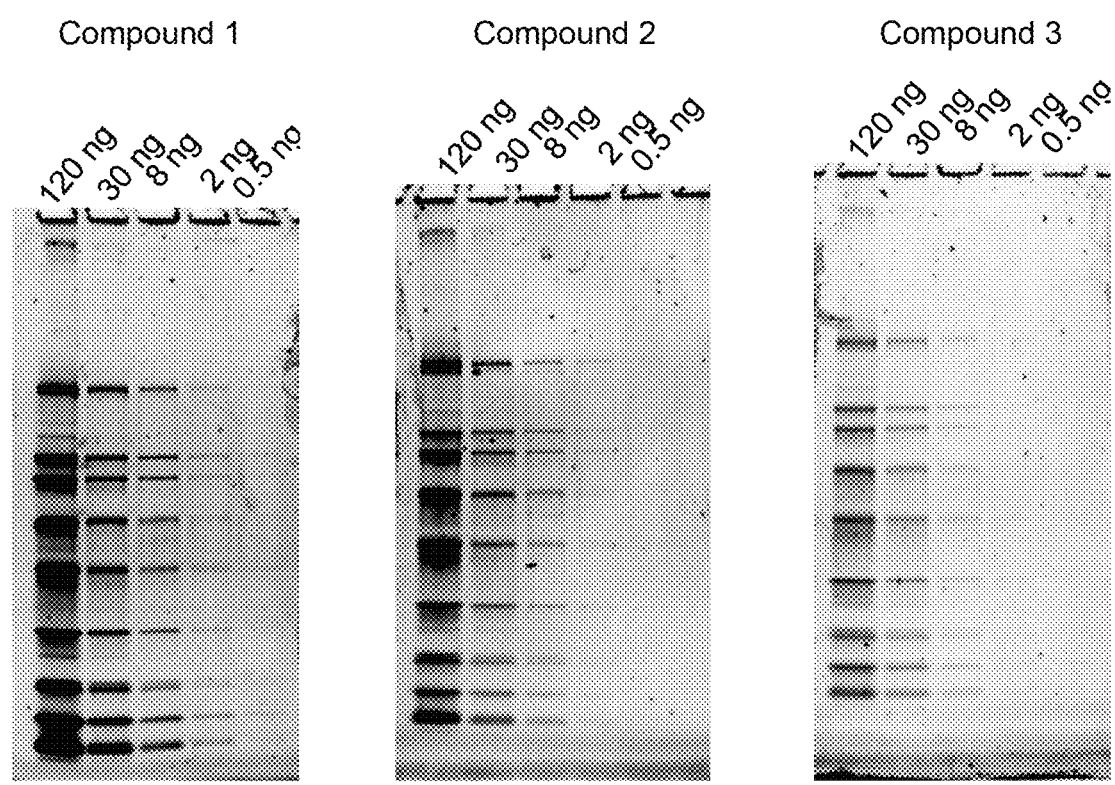
FIG. 3 shows the staining of SDS-PAGE separated poly (amino acids) at different loading amounts using compounds 1, 2 and 3. The quantities indicated along the top of the gel image refer to amount of protein per band.

In one example, dilutions of protein standards were run on SDS-PAGE (Bio-Rad Criterion 4-20% Tris-Cl). The gel was incubated in a 1:100 dilution of the stock solution described above in 40% methanol, 0.85% phosphoric acid for 90 min. The gel was imaged with the VersaDoc system (Bio-Rad) using a 5 s exposure through a 520 nm long pass filter (FIG. 3).

Example 6

Gel Stain Comparison for Compound 1 vs. SYPRO Ruby

A 100× stock solution of compound 1 was prepared by dissolving it in dimethyl sulfoxide to a concentration of 7.5 mg/ml and subsequently diluting 50-fold into 10% (w/v) aqueous Pluronic F127.

Dilutions of protein standards were run on SDS-PAGE (Bio-Rad Criterion 8-16% Tris-Cl). The gel was incubated in a 1:100 dilution of the stock solution described above in 40% methanol, 0.85% phosphoric acid for 90 min.

An identically loaded and run gel was stained with SYPRO Ruby (Invitrogen) according to manufacturers instructions (fixing twice for 30 min with 50% methanol, 7% acetic acid, staining overnight and destaining 30 min with 10% methanol, 7% acetic acid).

Figure 2:
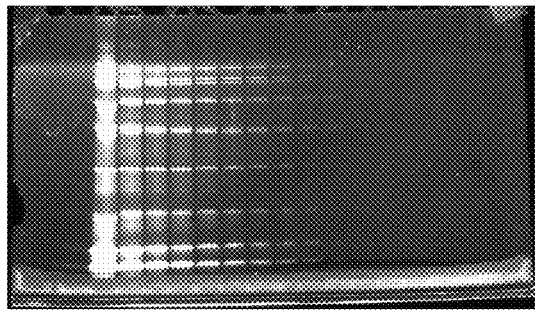
FIGS. 2A and 2B show images of gel stained with either Compound 1 or SYPRO Ruby.
Figure 2:
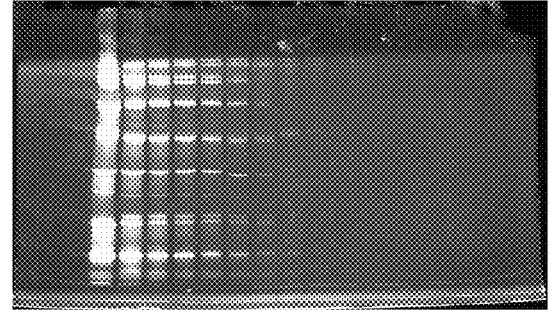
Figure 2:
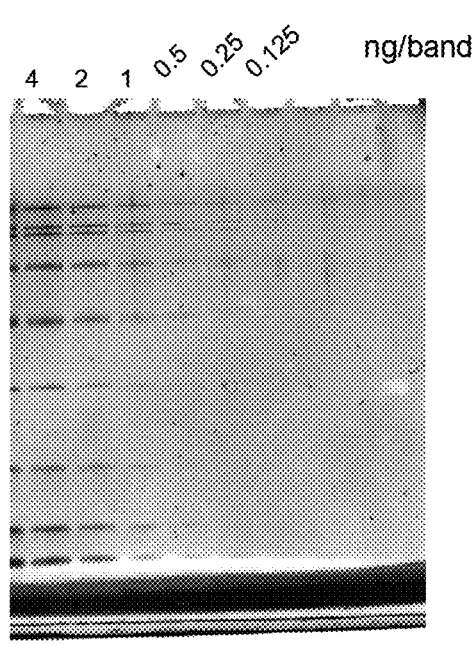
Figure 2:
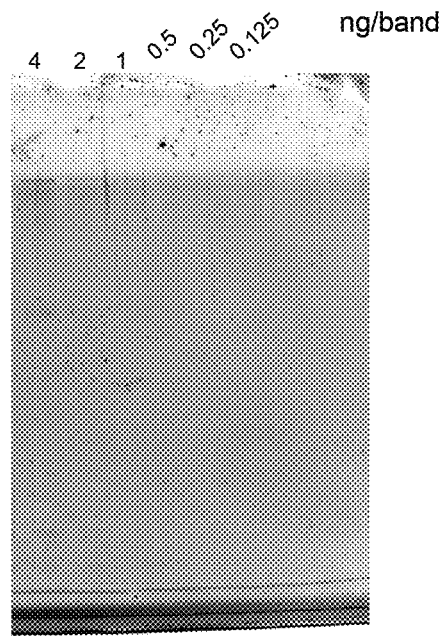

Both gels were imaged with the VersaDoc system (Bio-Rad) using a 101 exposure through a 520 nm longpass filter (FIG. 2).

Example 7

Time Course of Gel Staining with Compound 1

A 100× stock solution of compound 1 was prepared by dissolving it in dimethyl sulfoxide to a concentration of 7.5 mg/ml and subsequently diluting 50-fold into 10% (w/v) aqueous Pluronic F127.

Figure 4:
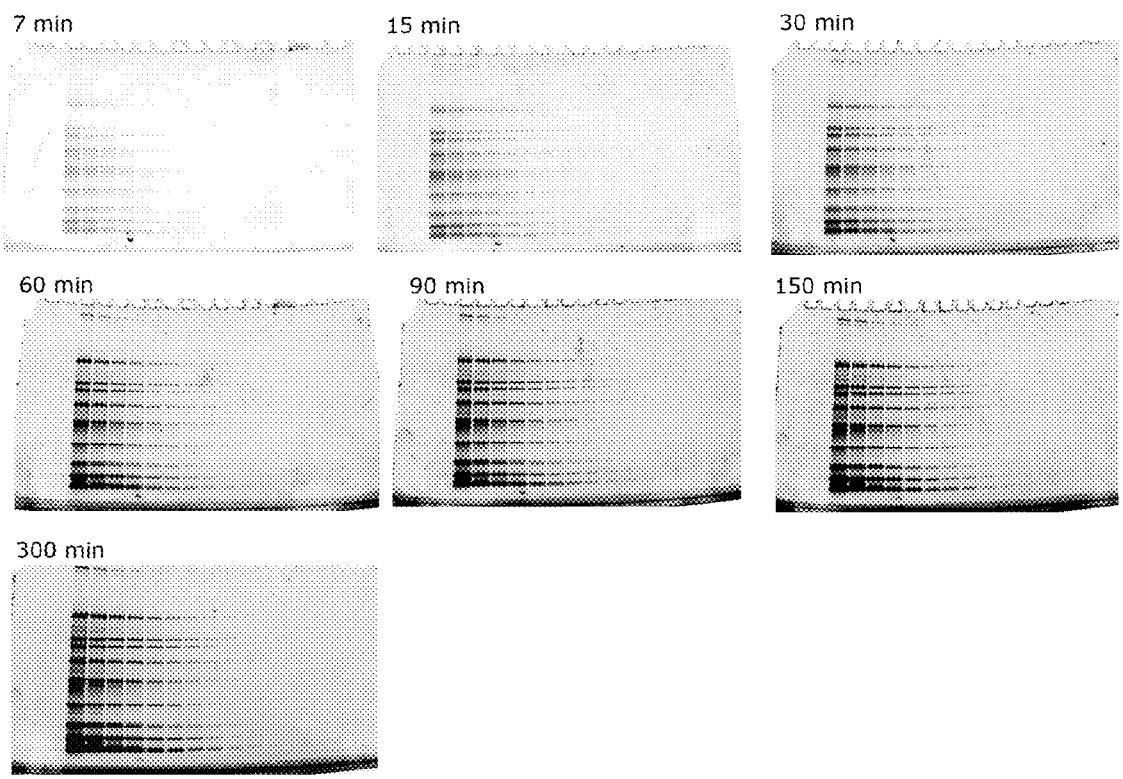
FIG. 4 shows the staining of protein standards using compound 1 showing maximum staining intensity at 90 minutes with no overstaining.

Dilutions of protein standards were run on SDS-PAGE (Bio-Rad Criterion 8-16% Tris-Cl). The gel was incubated in a 1:100 dilution of the stock solution described above in 40% methanol, 0.85% phosphoric acid. The gel was removed from this solution periodically, photographed with UV transillumination, and replaced in the solution. The gel was imaged in this manner after 7, 15, 30, 60, 90, 150 and 300 minutes of incubation. Results are shown in FIG. 4. Maximum staining intensity was achieved within 90 min and overstaining did not occur with more prolonged staining.

Example 8

Use of Compound 1 to Visualize 2-D PAGE Separation

Figure 5:
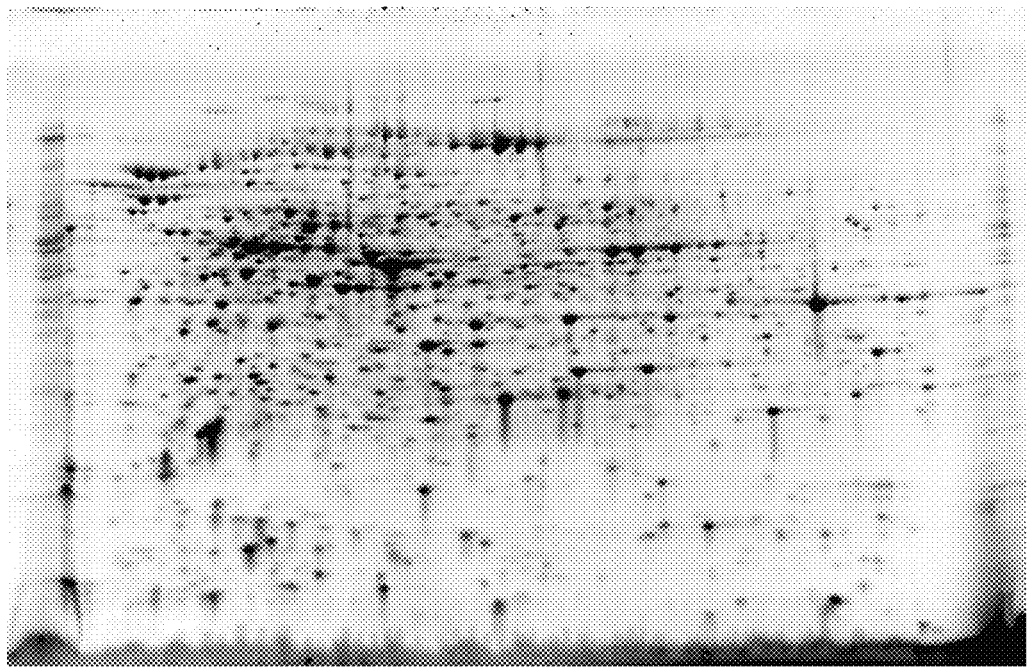
FIG. 5 shows the separation of E. coli lysate by 2-D electrophoresis with staining by compound 1 in 40% methanol, 0.85% phosphoric acid.

An *E. coli* lysate (40 μg of protein) was separated by 2-D electrophoresis (first dimension: 11 cm pH 5-8, second dimension: SDS-PAGE 8-16% acrylamide). The gel was stained and imaged as described in Examples 6 and 7. The result is shown in FIG. 5.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method of staining a poly(amino acid), comprising contacting the poly(amino acid) with a metal complex comprising:
   (i) at least one metal ion; and
   (ii) a plurality of donor ligands each fully coordinated to the metal ion and each independently selected from the group consisting of a nitrogen donor ligand and a cyclometalated donor ligand, wherein at least one of the donor ligands is a cyclometalated donor ligand;
   wherein:
   each nitrogen donor ligand comprises a heteroaryl ring system having from 10 to 40 ring atoms, wherein from 2 to 8 ring atoms are each independently selected from the group consisting of N, O and S, wherein at least two ring atoms are N, and wherein each nitrogen donor ligand is substituted with from 0 to 4 $R^1$ groups;
   each cyclometalated donor ligand is a member selected from the group consisting of:

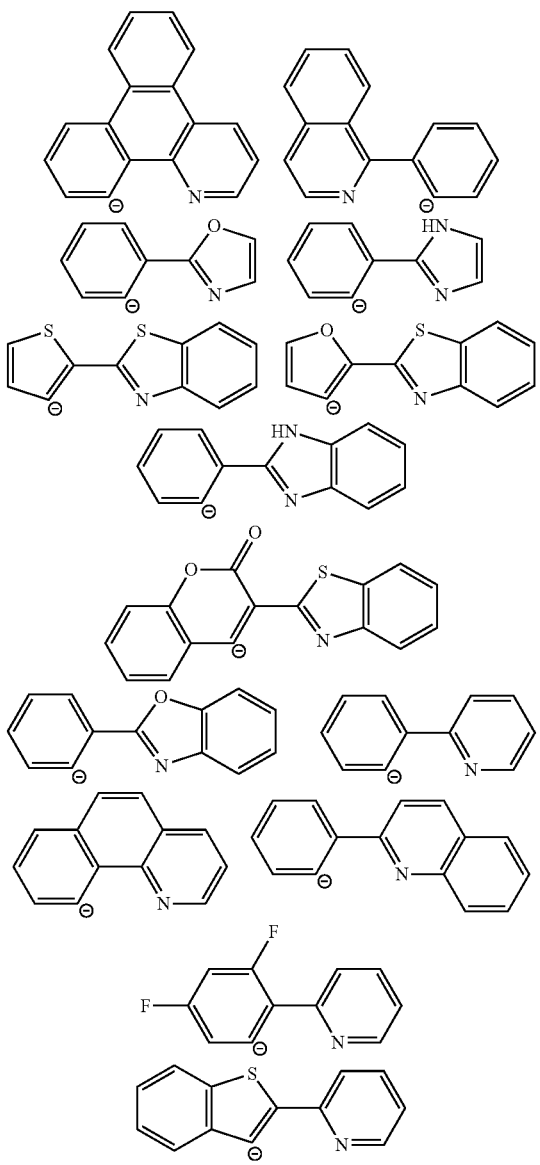

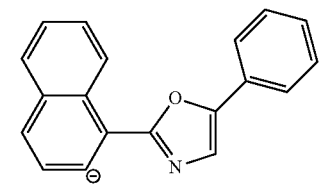

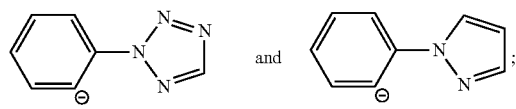

each $R^1$ is independently selected from the group consisting of $C_{1-6}$ alkyl, $C_{2-6}$ alkenyl, $C_{2-6}$ alkynyl, $C_{1-6}$ alkoxy, halogen, $C_{1-6}$ haloalkyl, —$OR^2$, —$NR^2R^3$, —CN, —$C(O)R^2$, —$OC(O)R^2$, —$C(O)NR^2R^3$, —$N(R^2)C(O)R^3$, —$OC(O)NR^2R^3$, —$NR^2C(O)NR^3R^4$, —$NR^2C(S)NR^3R^4$, —$NO_2$, =O, aryl, heteroaryl, cycloalkyl and heterocycloalkyl; and each $R^2$, $R^3$ and $R^4$ are independently selected from the group consisting of H and $C_{1-12}$ alkyl;

wherein the poly(amino acid) is present in a sample mixture on or in an SDS-PAGE gel, and wherein said metal complex is cationic in overall electronic charge, to achieve non-covalent association of said metal complex with the poly(amino acid) and to thereby stain the poly(amino acid).

2. The method of claim 1, wherein the metal complex comprises one nitrogen donor ligand and two cyclometalated donor ligands.

3. The method of claim 1, wherein each nitrogen donor ligand has the formula:

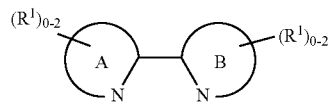

wherein rings A and B are each independently a heteroaryl ring system having from 5 to 20 ring atoms, where from 1 to 4 ring atoms of each of rings A and B are each independently selected from the group consisting of N, O and S, wherein at least one ring atom is N.

4. The method of claim 1, wherein each nitrogen donor ligand is a member selected from the group consisting of:

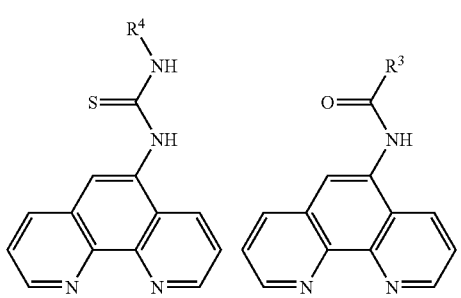

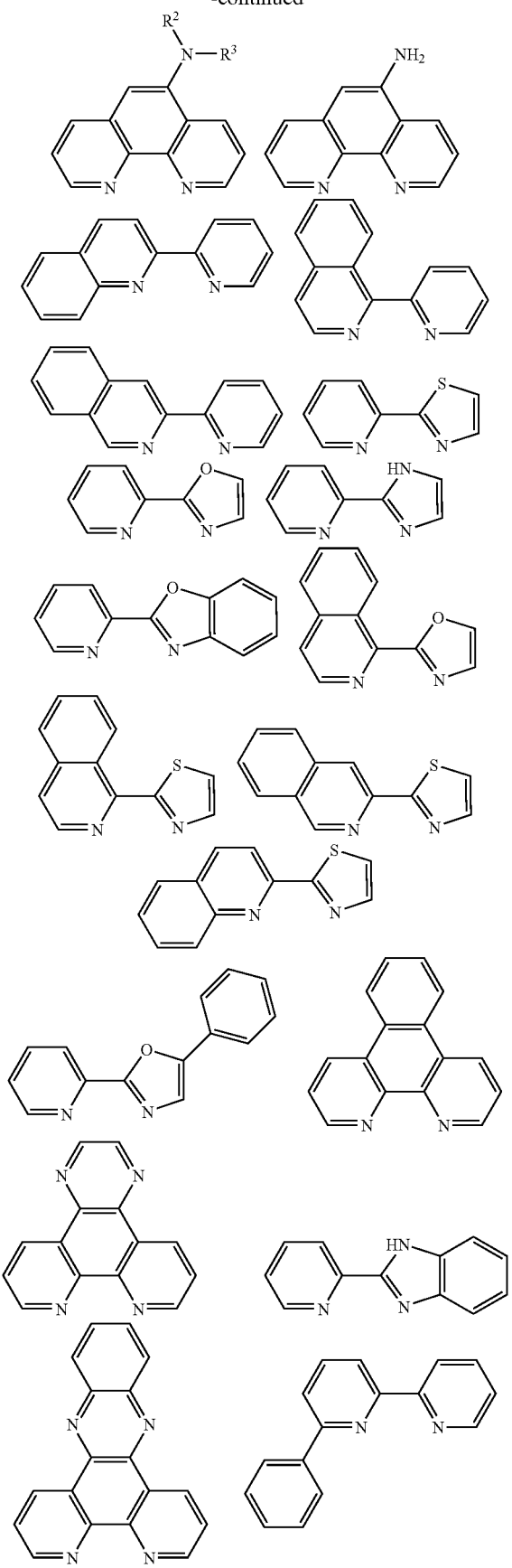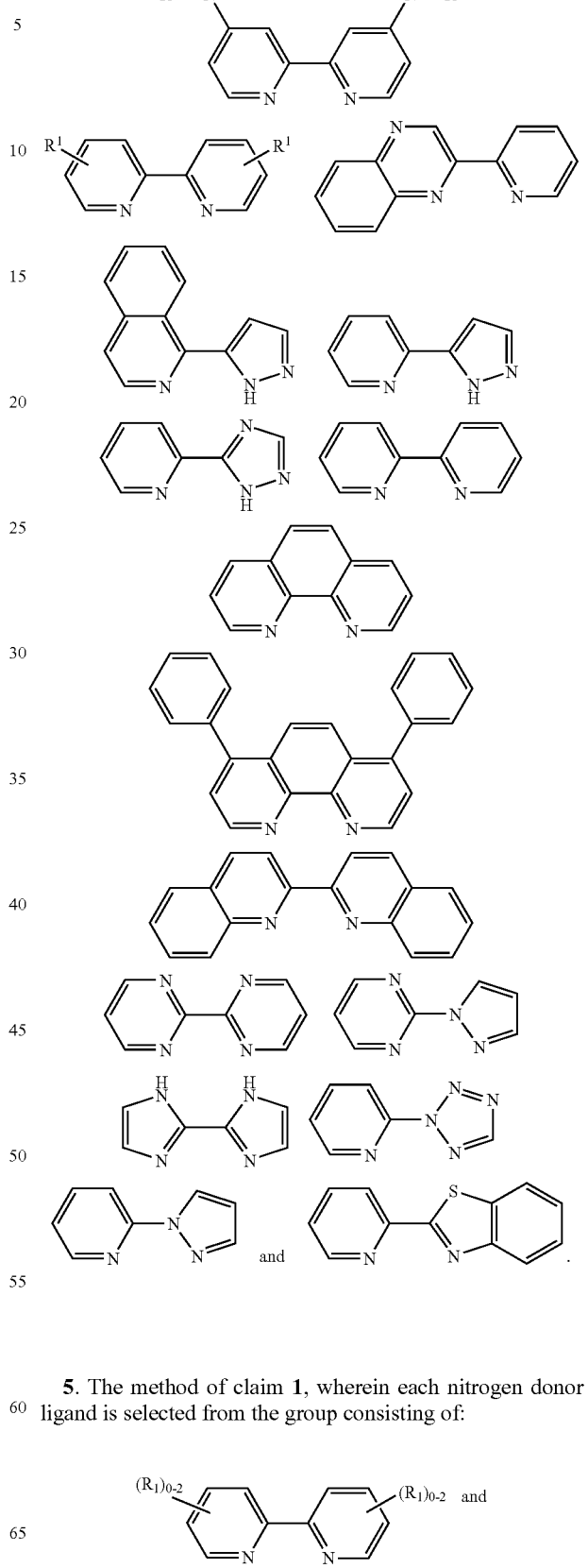
5. The method of claim 1, wherein each nitrogen donor ligand is selected from the group consisting of:
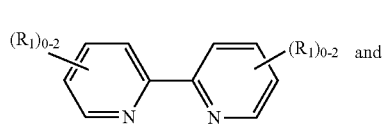

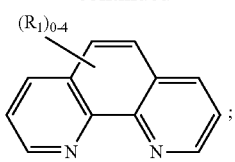

wherein each $R^1$ is independently selected from the group consisting of $C_{1-6}$ alkyl, —$NR^2R^3$, —$N(R^2)C(O)R^3$, —$NR^2C(O)NR^3R^4$, —$NR^2C(S)NR^3R^4$ and phenyl.

6. The method of claim 1, wherein the metal ion is a member selected from the group consisting of Ir, Rh, Os, Pt, Ru, Pd and Re.

7. The method of claim 6, wherein the metal ion is Ir(III).

8. The method of claim 1, wherein the metal complex is a member selected from the group consisting of:

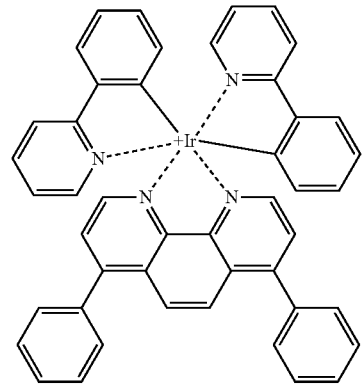

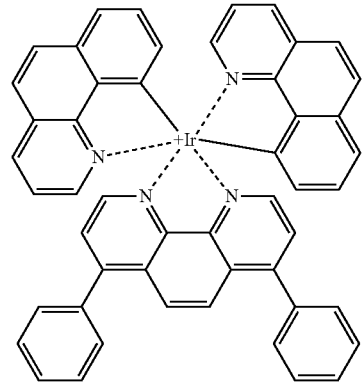

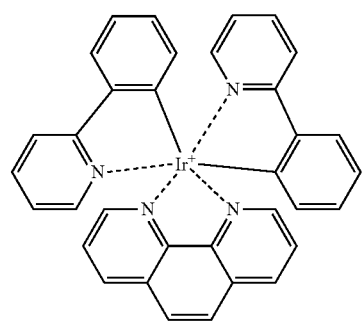

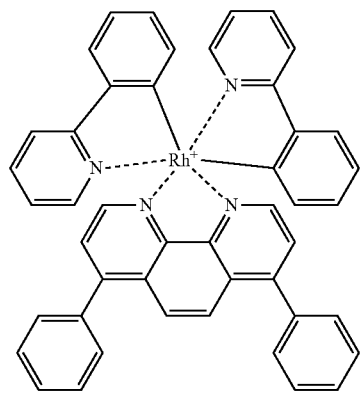

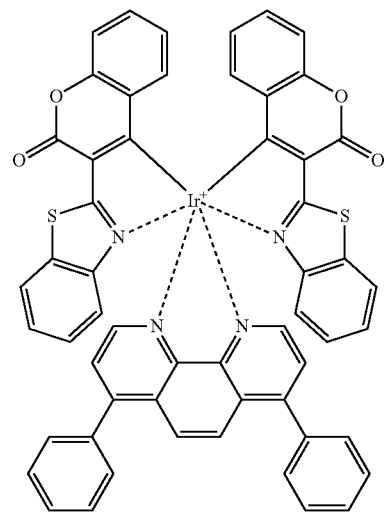

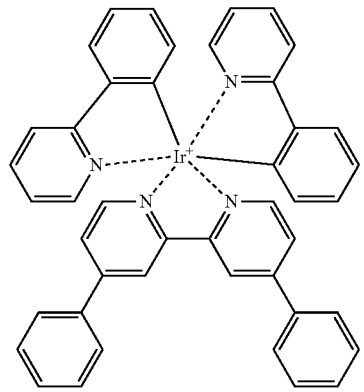

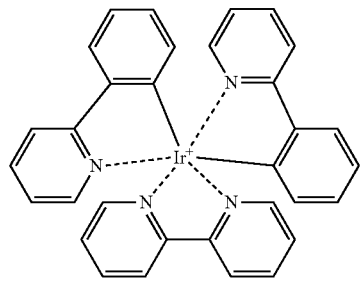

-continued
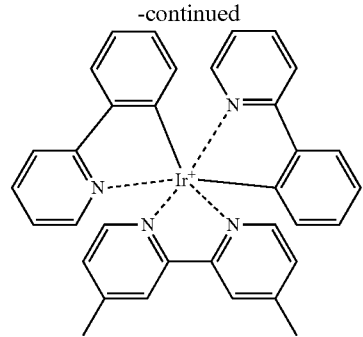
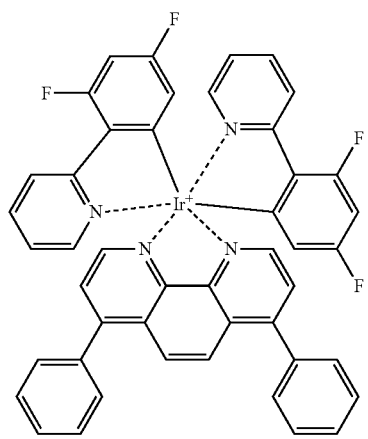
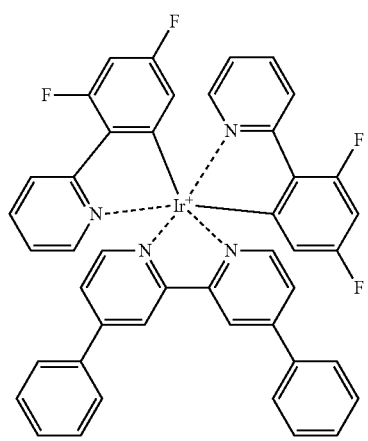
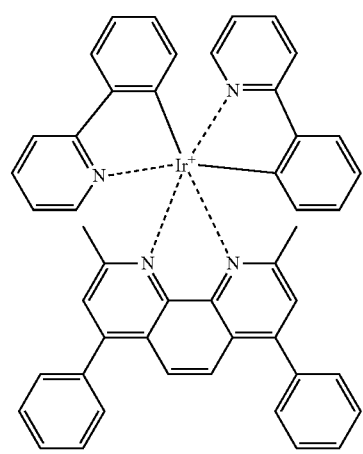
-continued
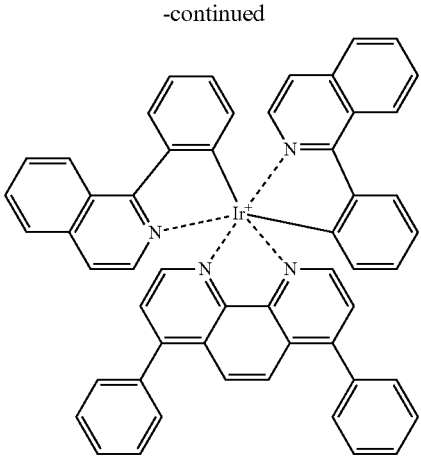
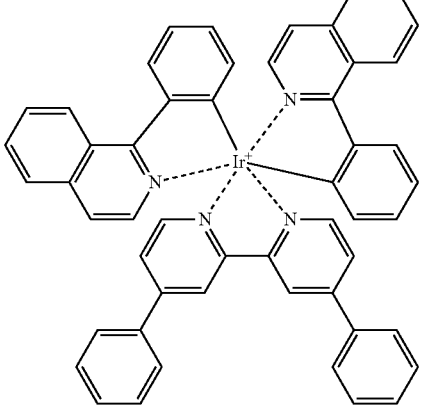
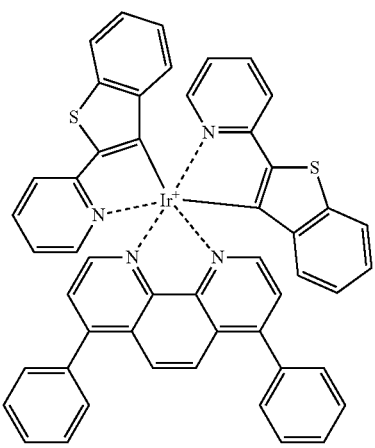
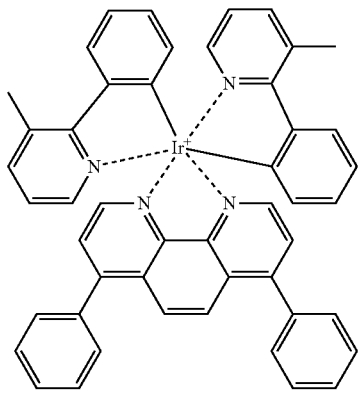

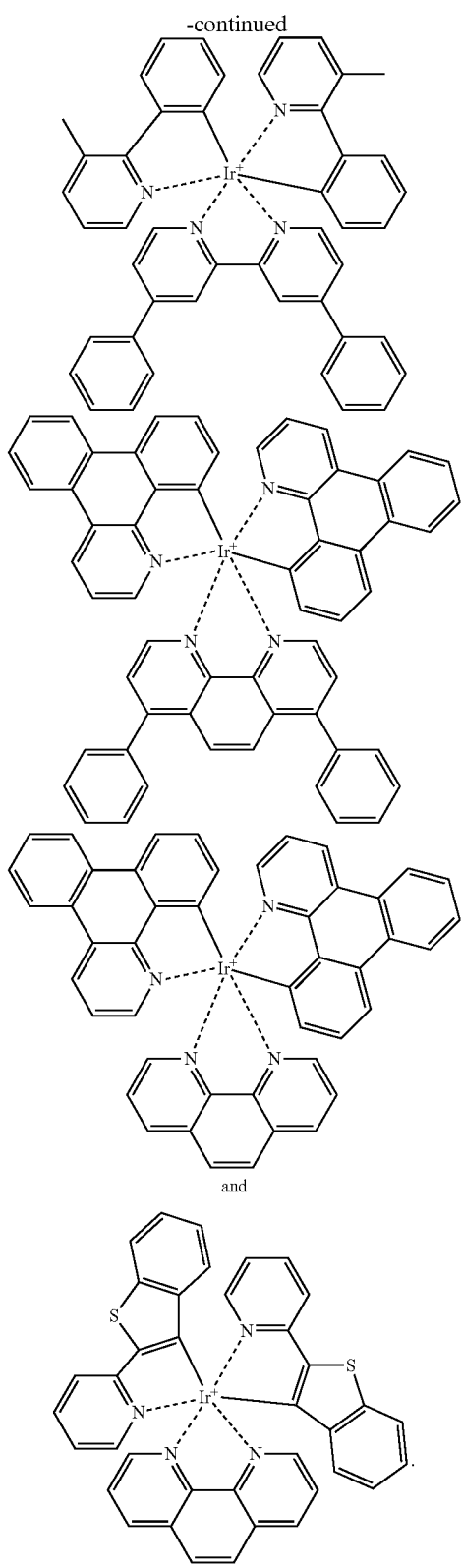
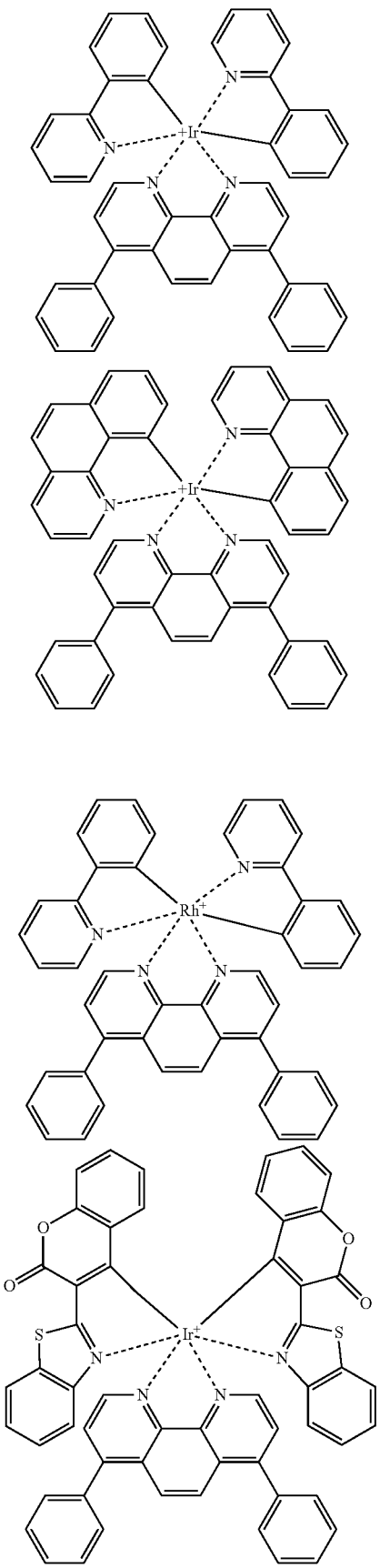
and
9. The method of claim 1, wherein the method is performed in the absence of de-staining the poly(amino acid).
10. The method of claim 1, wherein the method is performed in the absence of fixing the poly(amino acid).
11. The method of claim 1, wherein the metal complex is a member selected from the group consisting of:

51
-continued
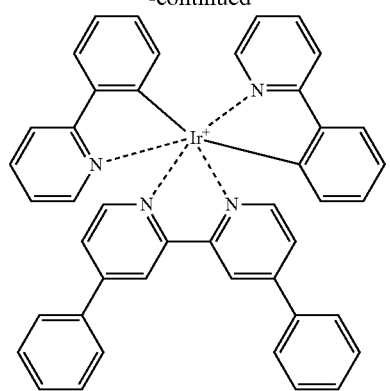
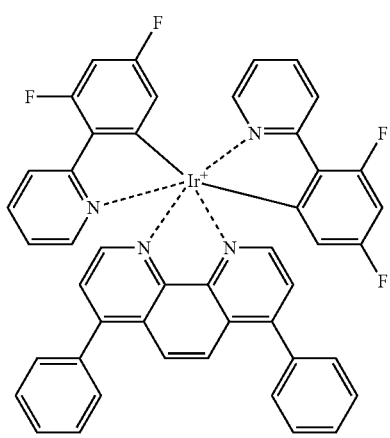
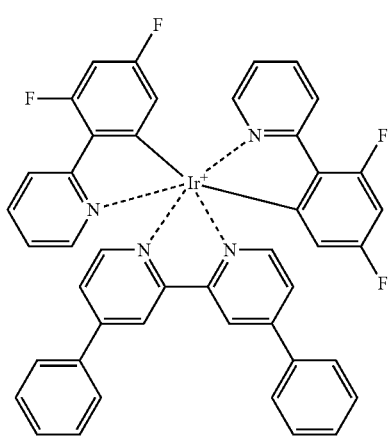
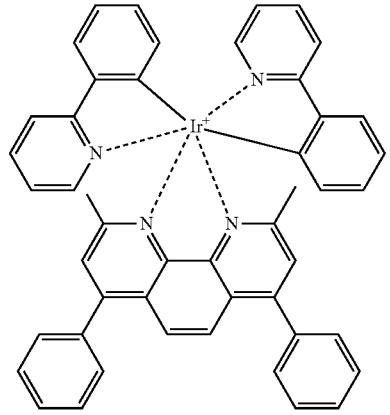
52
-continued
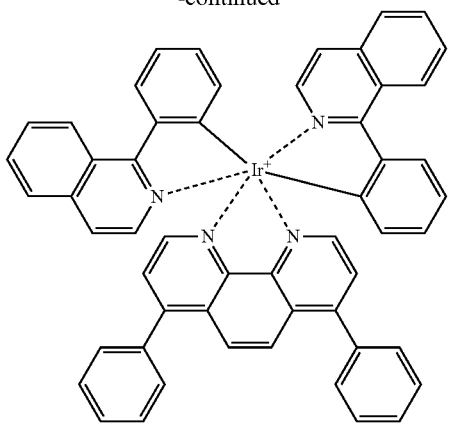
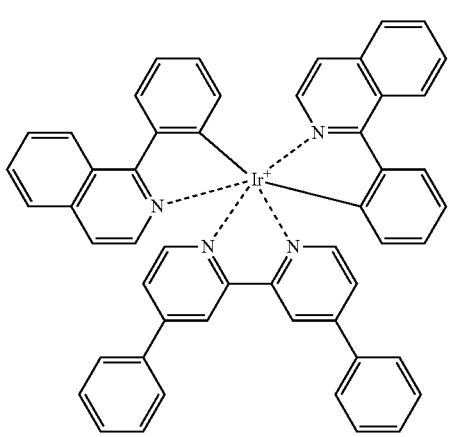
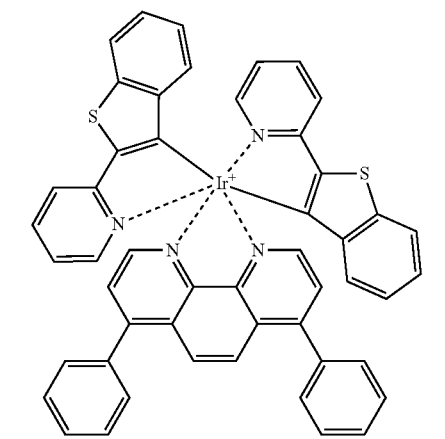
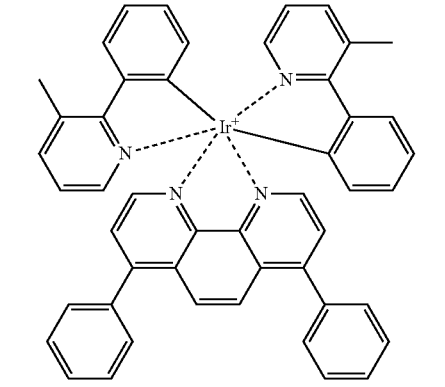

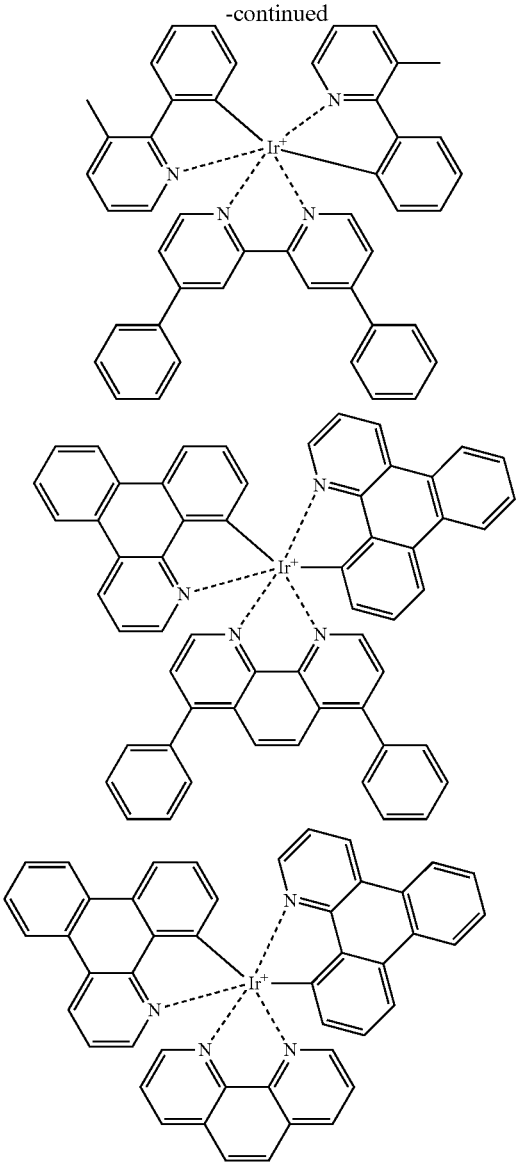
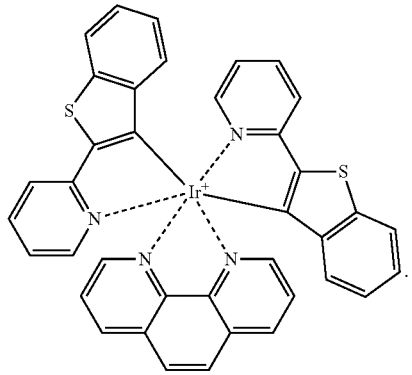
12. The method of claim 1, wherein the metal complex is
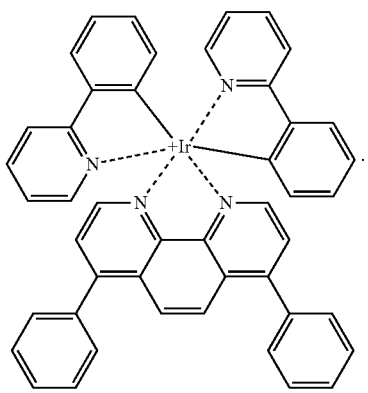
* * * * *